(12) United States Patent
Ishii et al.

(10) Patent No.: US 10,993,690 B2
(45) Date of Patent: May 4, 2021

(54) MEDICAL APPARATUS AND X-RAY SYSTEM

(71) Applicant: CANON MEDICAL SYSTEMS CORPORATION, Otawara (JP)

(72) Inventors: Shigeyuki Ishii, Nasushiobara (JP); Takuma Igarashi, Nasushiobara (JP); Hayato Konishi, Otawara (JP); Takeshi Ezumi, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 141 days.

(21) Appl. No.: 16/016,905

(22) Filed: Jun. 25, 2018

(65) Prior Publication Data

US 2018/0368800 A1   Dec. 27, 2018

(30) Foreign Application Priority Data

Jun. 26, 2017   (JP) .............................. JP2017-124209

(51) Int. Cl.
*A61B 6/00* (2006.01)
*G01T 1/17* (2006.01)
(Continued)

(52) U.S. Cl.
CPC .............. *A61B 6/542* (2013.01); *A61B 6/107* (2013.01); *A61B 6/4291* (2013.01);
(Continued)

(58) Field of Classification Search
CPC ....... A61B 6/542; A61B 6/107; A61B 6/4291; A61B 6/4441; A61B 6/465; A61B 6/504; G01T 1/17; G01T 1/2907; G01T 1/2914
See application file for complete search history.

(56) References Cited

U.S. PATENT DOCUMENTS

| 5,873,826 A | * | 2/1999 | Gono | ..................... A61B 6/032 |
| | | | | 600/425 |
| 2009/0161827 A1 | * | 6/2009 | Gertner | ................ A61N 5/1017 |
| | | | | 378/65 |

(Continued)

FOREIGN PATENT DOCUMENTS

| JP | 2009160309 A | * | 7/2009 | ............... A61N 5/10 |
| JP | 2013183811 A | * | 9/2013 | ............... A61N 5/10 |

(Continued)

OTHER PUBLICATIONS

Oyu et al.—JP 2009-160309 A—Google Patents English Translation obtained Jan. 14, 2020 (Year: 2020).*

(Continued)

*Primary Examiner* — David P Porta
*Assistant Examiner* — Jeremy S Valentiner
(74) *Attorney, Agent, or Firm* — Oblon, McClelland, Maier & Neustadt, L.L.P.

(57) ABSTRACT

A medical apparatus according to an embodiment includes control circuitry. The control circuitry is configured to: acquire a three-dimensional cumulative dose distribution of an object; set a treatment target site by treatment accompanied with X-ray irradiation to the object; and determine an X-ray irradiating direction for performing the X-ray irradiation based on the three-dimensional cumulative dose distribution and the treatment target site.

15 Claims, 21 Drawing Sheets

(51) Int. Cl.
*G01T 1/29* (2006.01)
*A61B 6/10* (2006.01)

(52) U.S. Cl.
CPC ............ *A61B 6/4441* (2013.01); *A61B 6/465* (2013.01); *A61B 6/504* (2013.01); *G01T 1/17* (2013.01); *G01T 1/2907* (2013.01); *G01T 1/2914* (2013.01)

(56) References Cited

U.S. PATENT DOCUMENTS

| | | | | |
|---|---|---|---|---|
| 2013/0243165 A1* | 9/2013 | Bourdeaux | ............ | G16H 40/63 378/165 |
| 2016/0113608 A1 | 4/2016 | Abe et al. | | |
| 2016/0114187 A1* | 4/2016 | Ishii | ..................... | A61N 5/1031 378/42 |
| 2020/0000418 A1* | 1/2020 | Padoy | ..................... | A61B 6/542 |

FOREIGN PATENT DOCUMENTS

| | | |
|---|---|---|
| JP | 2015-500119 A | 1/2015 |
| JP | 2016-77795 | 5/2016 |

OTHER PUBLICATIONS

Yokota et al.—JP 2013-183811 A—Google Patents English Translation obtained Jan. 14, 2020 (Year: 2020).*

Japanese Office Action dated Feb. 24, 2021, issued in Japanese Patent Application No. 2017-124209.

* cited by examiner

| INDEX | X-RAY IRRADIATING DIRECTION | | PRIMARY SUITABILITY LEVEL OF EACH INDEX (SCORE / 10 POINTS) | PRIMARY SUITABILITY LEVEL OF EACH INDEX (NORMALIZATION) |
|---|---|---|---|---|
| | ROTATION ANGLE OF LEFT-RIGHT DIRECTION | ROTATION ANGLE OF CRANIAL DIRECTION | | |
| CUMULATIVE DOSE OF PATIENT | −180° | −180° | 9 | 0.9 |
| | ... | ... | ... | ... |
| | +175° | +175° | 8 | 0.8 |
| VISIBILITY OF TREATMENT TARGET SITE | −180° | −180° | 6 | 0.6 |
| | ... | ... | ... | ... |
| | +175° | +175° | 6 | 0.6 |
| EXPOSURE DOSE OF SURROUNDING PERSON | −180° | −180° | 7 | 0.7 |
| | ... | ... | ... | ... |
| | +175° | +175° | 9 | 0.9 |

FIG. 7

| X-RAY IRRADIATING DIRECTION | | SECONDARY SUITABILITY LEVEL OF OVERALL INDEXES (SCORE / 30 POINTS) | SECONDARY SUITABILITY LEVEL OF OVERALL INDEXES (NORMALIZATION) |
|---|---|---|---|
| ROTATION ANGLE OF LEFT-RIGHT DIRECTION | ROTATION ANGLE OF CRANIAL DIRECTION | | |
| −180° | −180° | 22 (9+6+7) | 0.73 (22/30) |
| ... | ... | ... | ... |
| +175° | +175° | 23 (8+6+9) | 0.77 (23/30) |

FIG. 8

MEDICAL APPARATUS AND X-RAY SYSTEM

CROSS-REFERENCE TO RELATED APPLICATION

This application is based upon and claims the benefit of priority from Japanese Patent Application No. 2017-124209, filed on Jun. 26, 2017, the entire contents of which are incorporated herein by reference.

FIELD

An embodiment as an aspect of the present invention relates to a medical apparatus and an X-ray system.

BACKGROUND

In recent years, a dose tracking system (DTS) has been developed that visualizes a cumulative dose (exposed dose) due to radiation irradiation, when performing a treatment on the treated region while irradiating the region including the treated region of the patient. This system displays, sequentially (in real time), the cumulative dose totalized from the start of the radiation irradiating manipulation to the present time.

As a procedure of a treatment accompanied with the X-ray irradiation, treatment of arteriovenous malformation (AVM), carotid artery stenting (CAS), coiling corresponding to unruptured cerebral artery aneurysm, coronary artery percutaneous coronary intervention (PCI), transcatheter aortic valve replacement (TAVR), and transcatheter arterial chemo-embolization (TACE) and the like can be mentioned.

The planning apparatus of the prior art can determine the X-ray irradiating direction in consideration of the cumulative dose of the patient using the DTS at the time of treatment planning.

BRIEF DESCRIPTION OF THE DRAWINGS

In accompanying drawings,

FIG. 7 is a table showing a primary suitability level of each index corresponding to each X-ray irradiating direction in the X-ray system according to the first embodiment;

FIG. 8 is a table showing a secondary suitability level of overall indexes corresponding to each X-ray irradiating direction in the X-ray system according to the first embodiment;

Figure 13A:
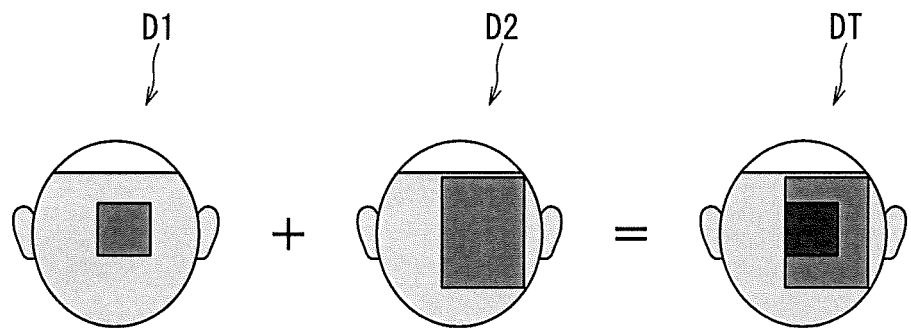
Figure 13B:
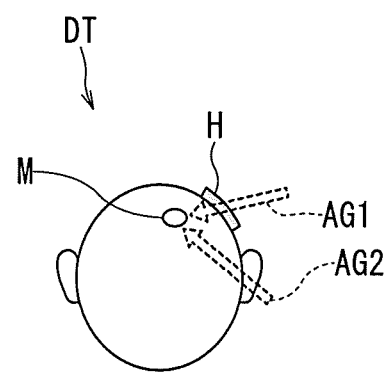
Figure 14B:
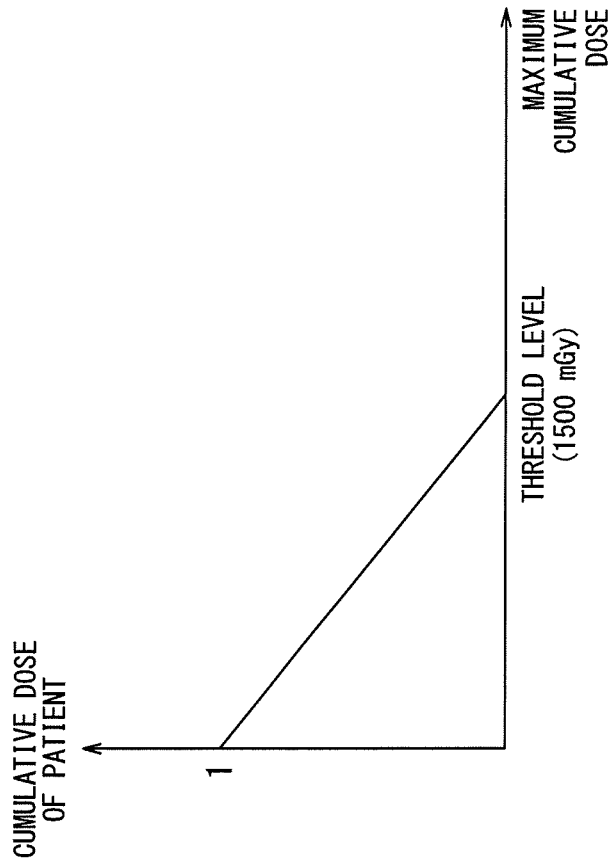
Figure 14A:
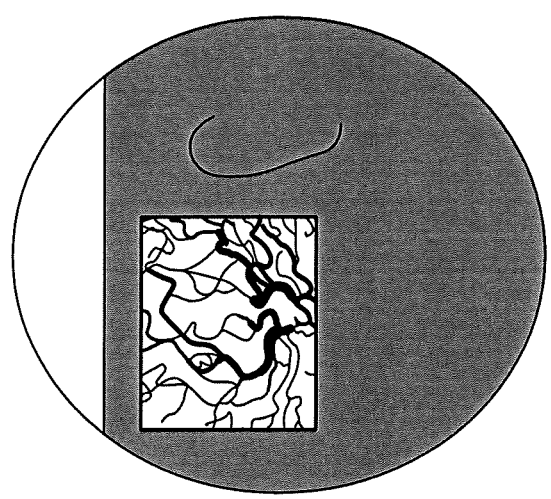
Figure 15:
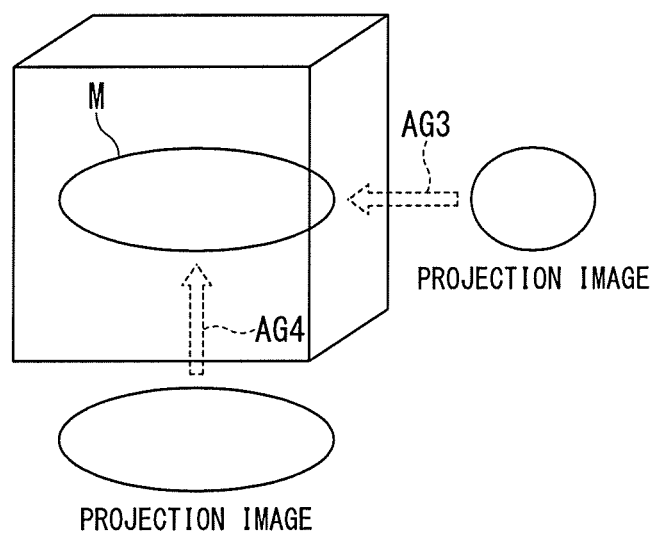
Figure 16A:
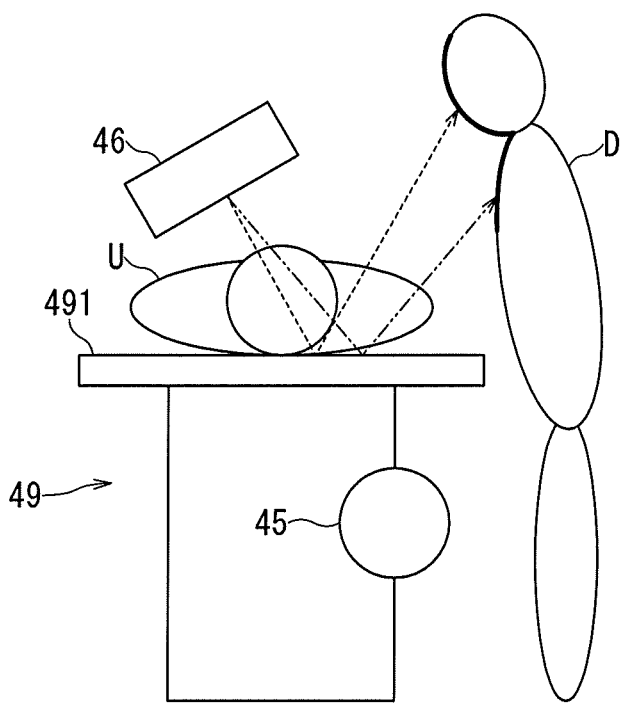
Figure 16B:
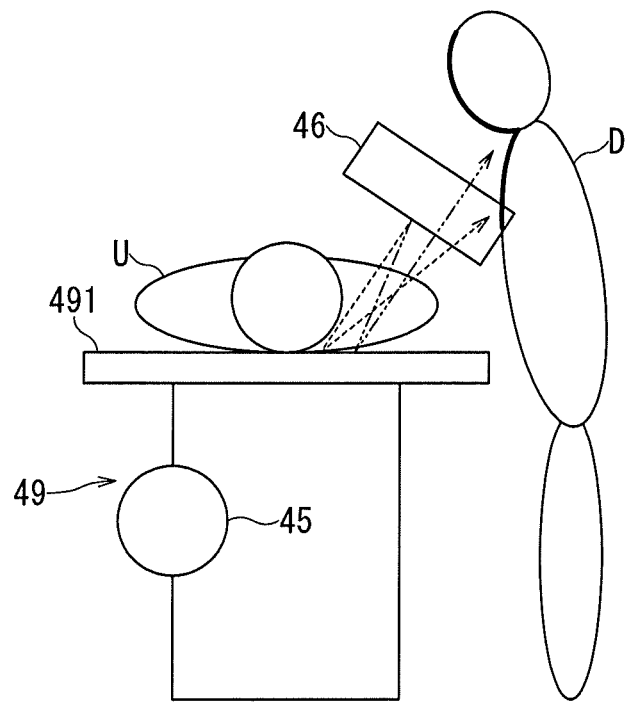
Figure 17:
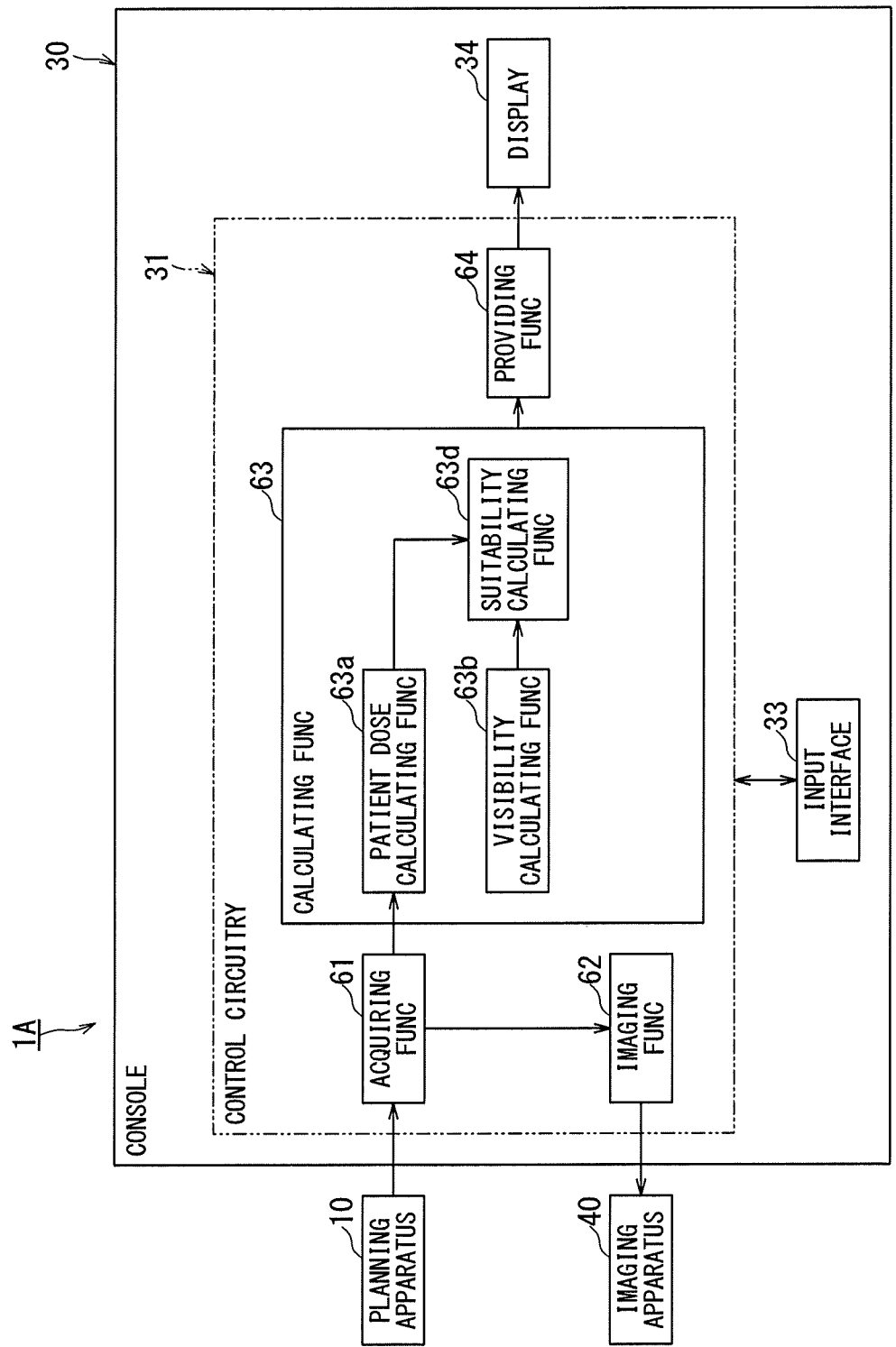
Figure 18:
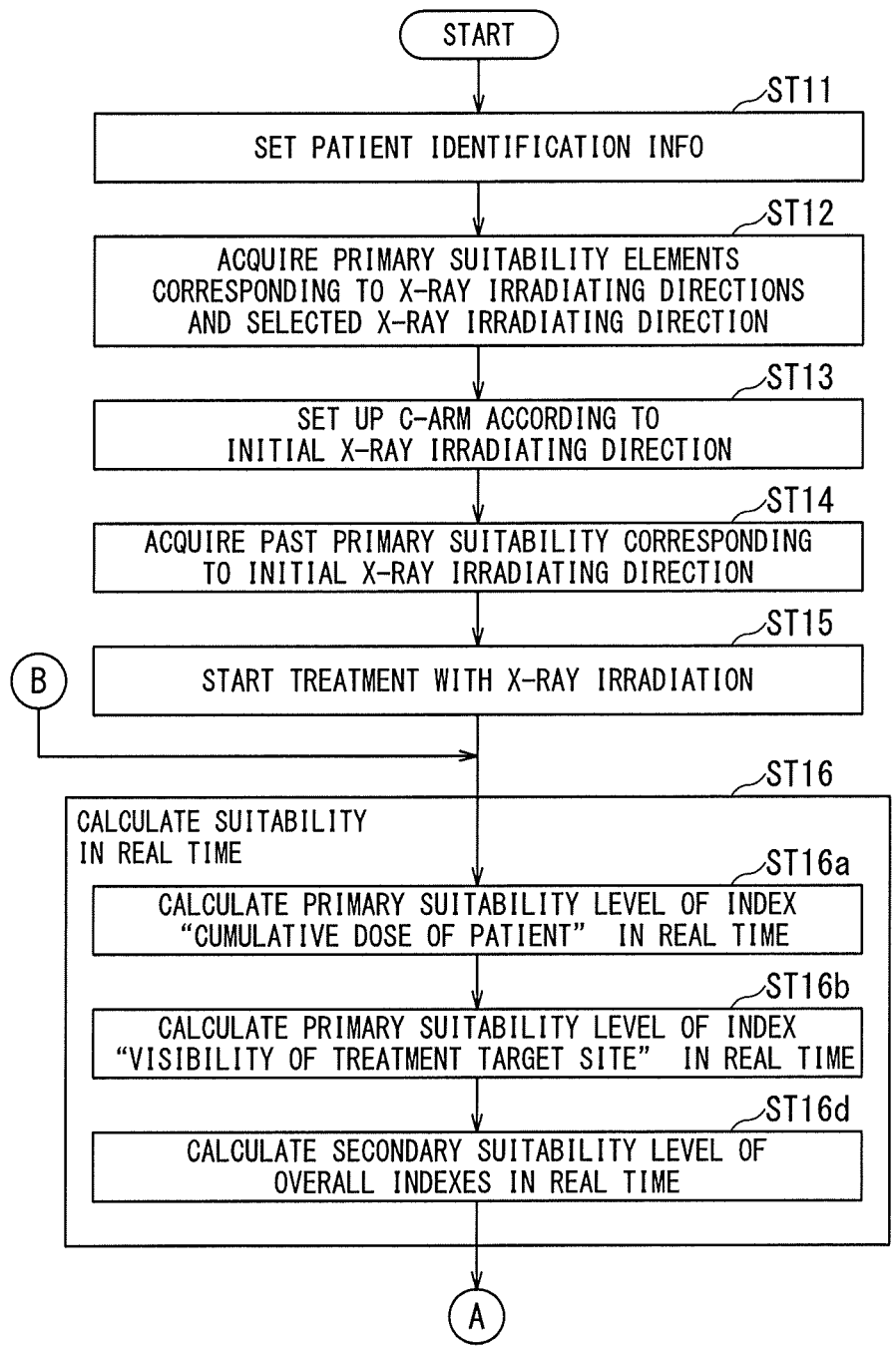
Figure 19:
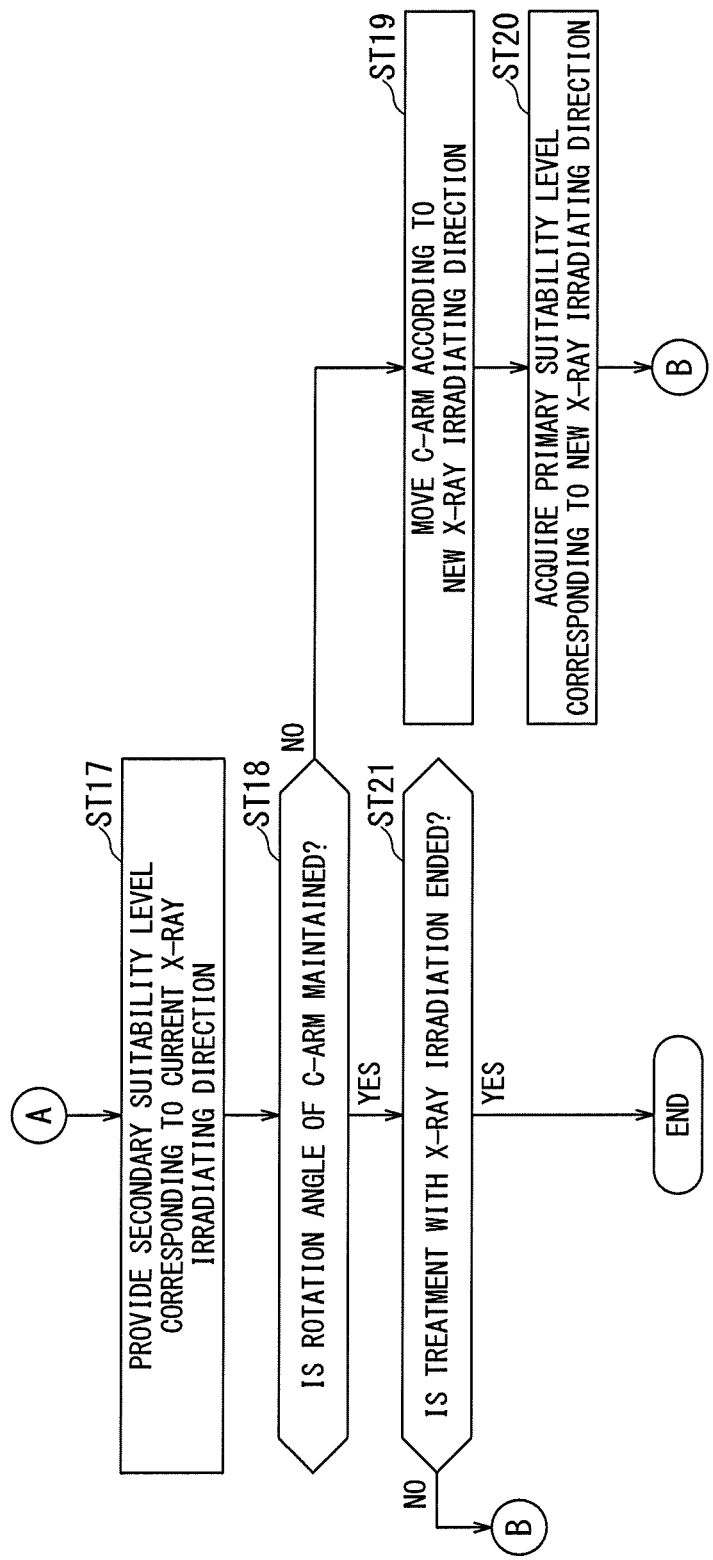
Figure 20A:
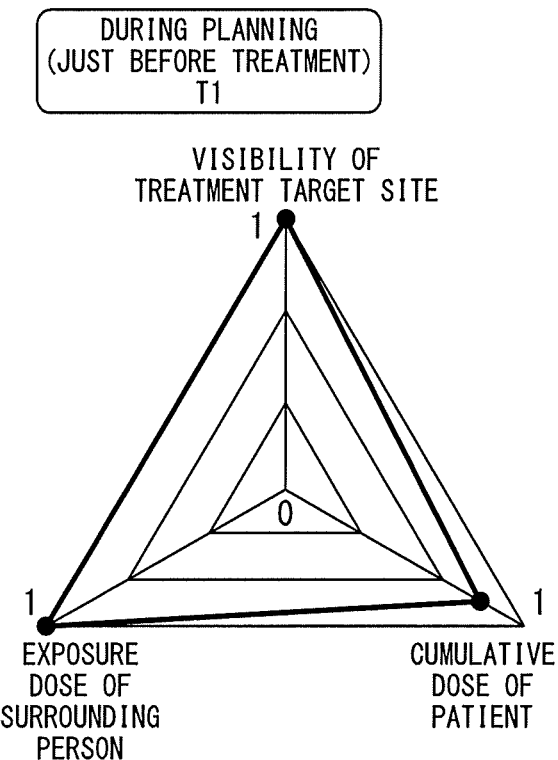
Figure 20B:
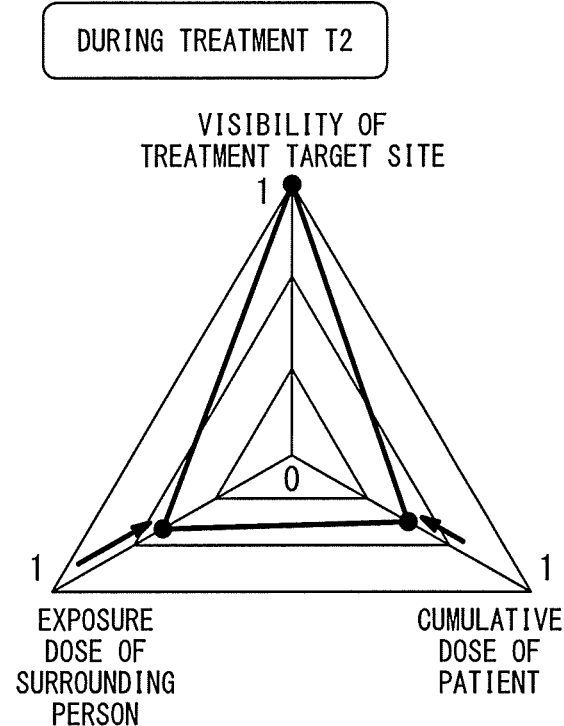
Figure 20C:
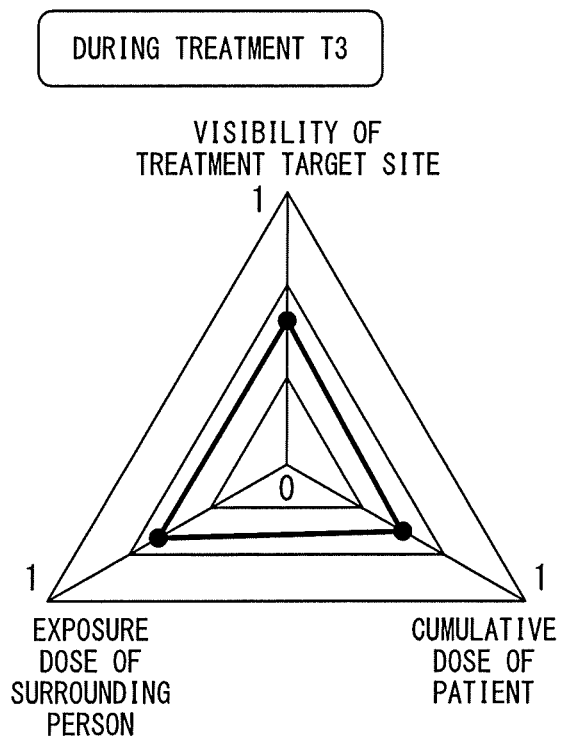
Figure 20D:
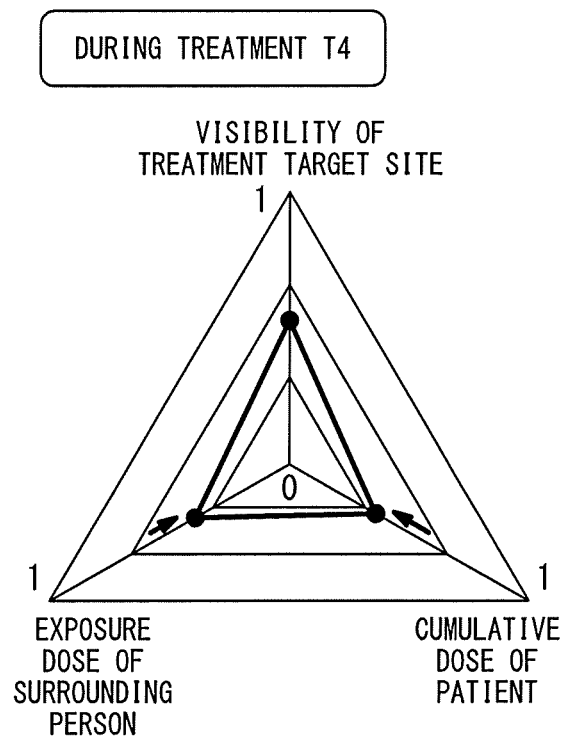
Figure 21:
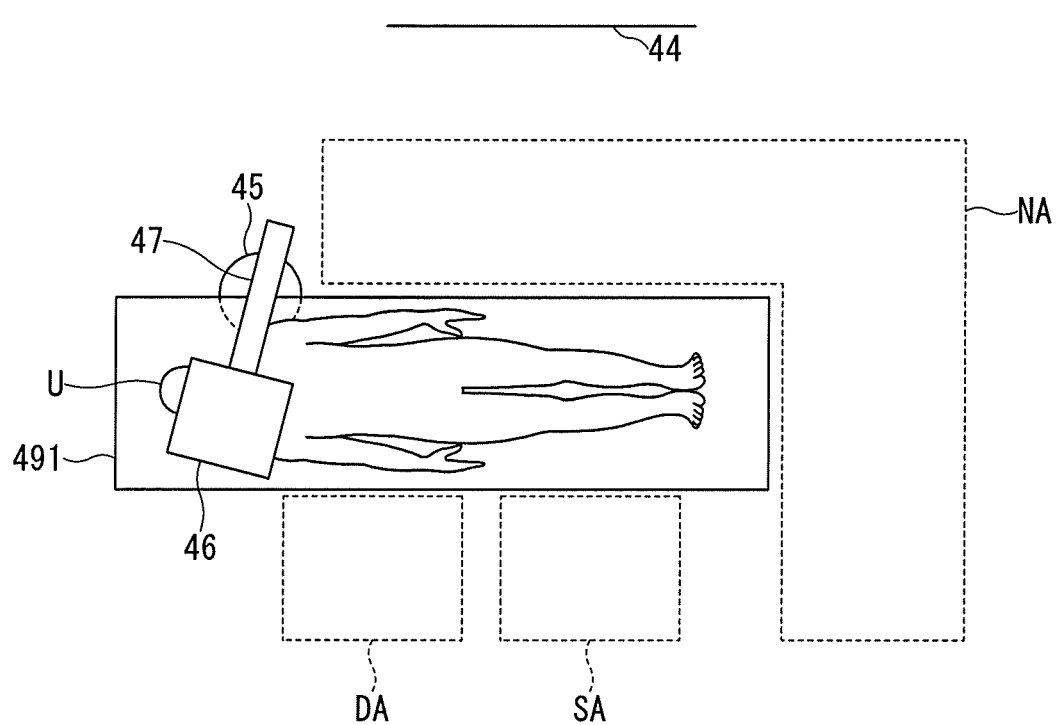

Each of FIGS. 13A and 13B is a diagram for explaining a method of calculating the primary suitability level of an index "cumulative dose of patient" in the X-ray system according to the first embodiment;

FIGS. 14A and 14B are diagrams for explaining a method of calculating the primary suitability of the index "cumulative dose of patient" in the X-ray system according to the first embodiment;

FIG. 15 is a diagram for explaining a method of calculating the primary suitability level of the index "visibility of treatment target site" in the X-ray system according to the first embodiment; Each of FIGS. 16A and 16B is a diagram for explaining a method of calculating the primary suitability level of the index "exposure dose of surrounding person" in the X-ray system according to the first embodiment;

FIG. 17 is a block diagram showing functions of an X-ray system according to a second embodiment;

The whole of FIGS. 18 and 19 is a flowchart showing an operation of the X-ray system according to the second embodiment;

Each of FIGS. 20A to 20D is a diagram showing a display example of the primary suitability level corresponding to the current X-ray irradiating direction in the X-ray system according to the second embodiment; and FIG. 21 is a top view showing a movement space of a surrounding person in a modified example of the X-ray systems according to the first and second embodiments.

DETAILED DESCRIPTION

A medical apparatus and an X-ray system according to an embodiment are described with reference to the accompanying drawings.

A medical apparatus according to an embodiment includes control circuitry. The control circuitry is configured to: acquire a three-dimensional cumulative dose distribution of an object; set a treatment target site by treatment accompanied with X-ray irradiation to the object; and determine an X-ray irradiating direction for performing the X-ray irradiation based on the three-dimensional cumulative dose distribution and the treatment target site.

1. First Embodiment

Figure 1:
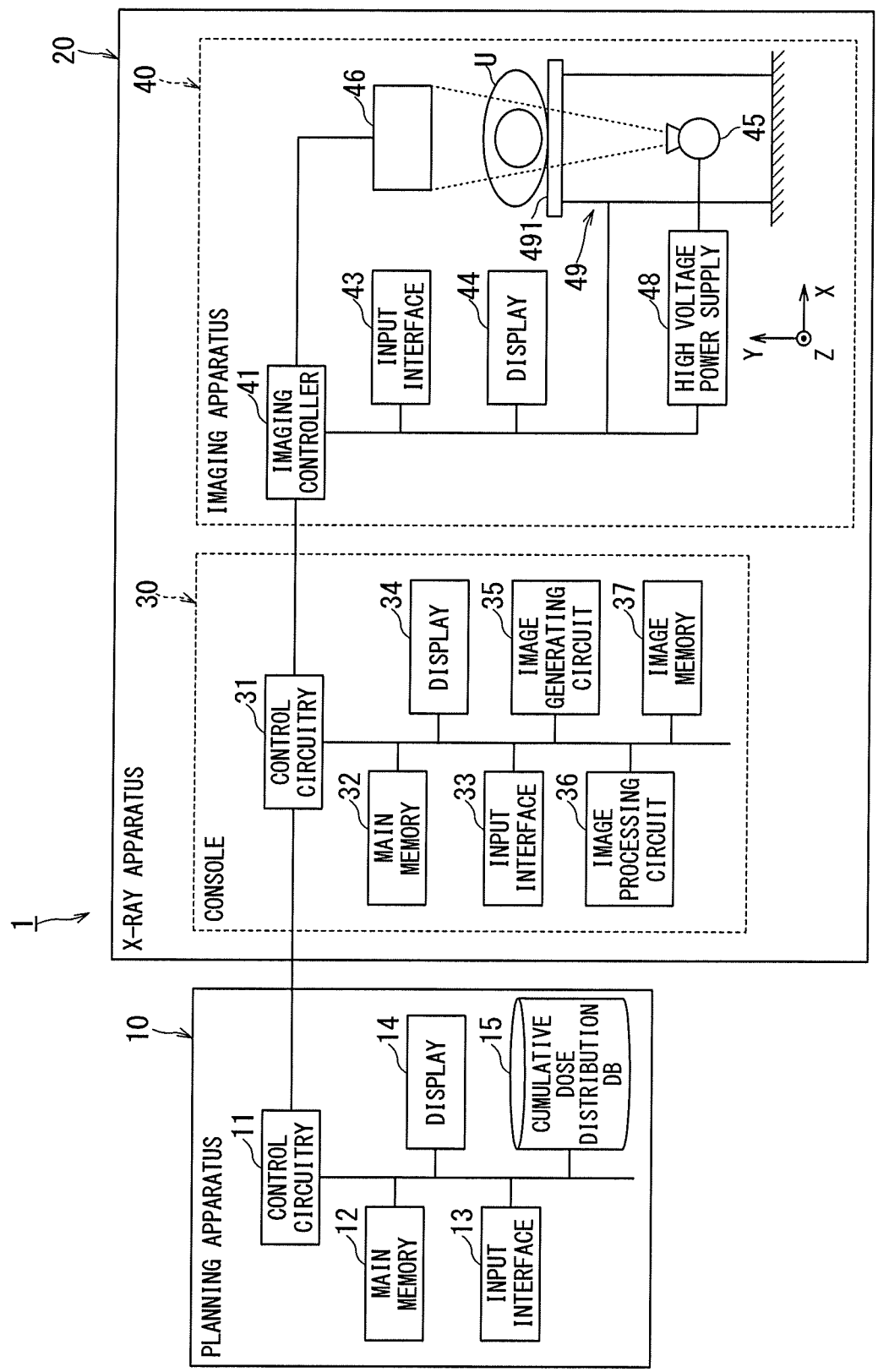
FIG. 1 is a schematic diagram showing a configuration of an X-ray system according to a first embodiment.
Figure 2:
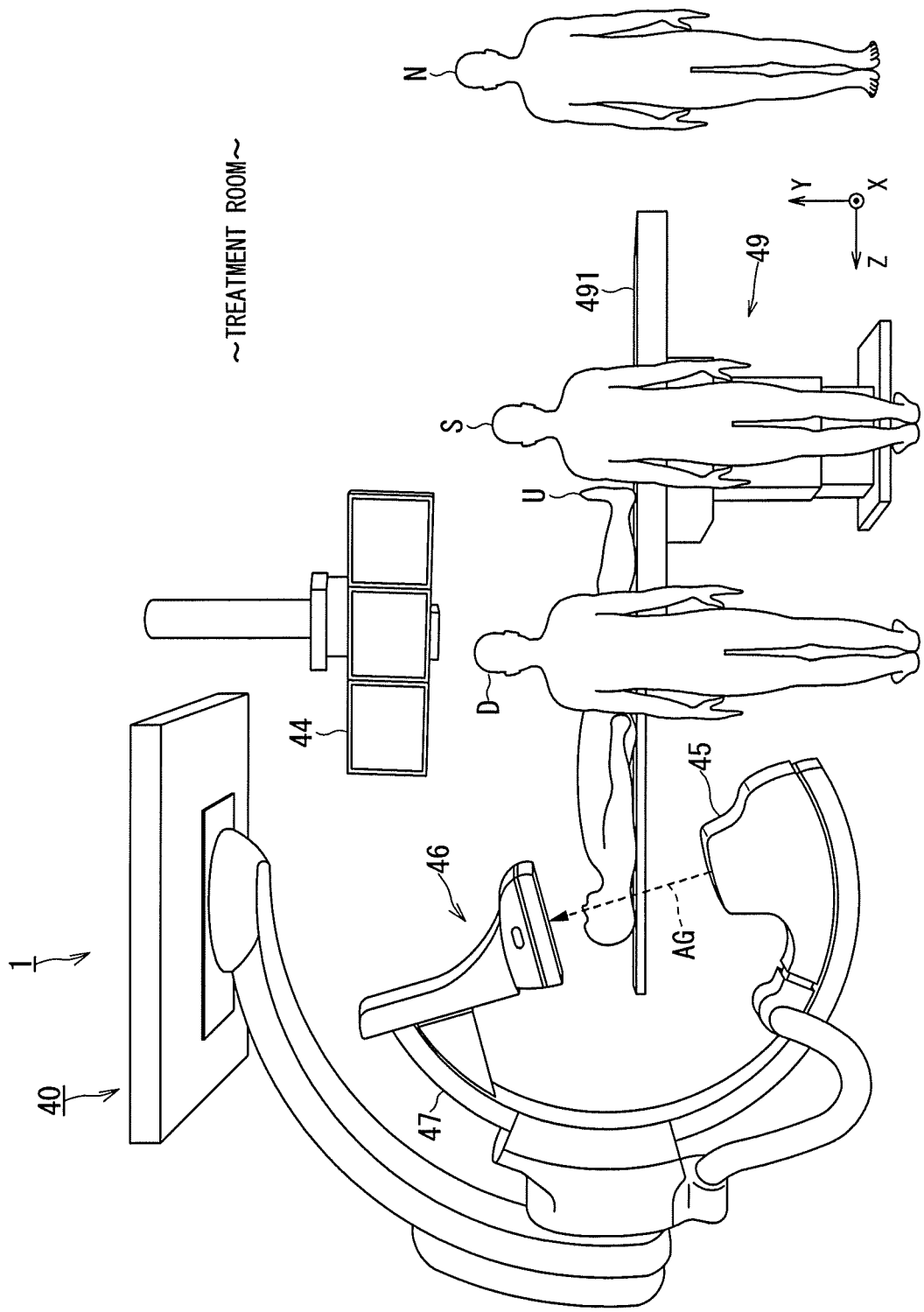
FIG. 2 is a perspective view showing an appearance of an imaging apparatus provided in the X-ray system according to the first embodiment.

FIG. 1 is a schematic diagram showing a configuration of an X-ray system according to a first embodiment. FIG. 2 is a perspective view showing an appearance of an imaging apparatus provided in the X-ray system according to the first embodiment.

FIGS. 1 and 2 show an X-ray system 1 according to a first embodiment. The X-ray system 1 includes a planning apparatus 10 and an X-ray apparatus 20. The planning apparatus 10 is installed outside a treatment room and a control room. The X-ray apparatus 20 is an apparatus such as an angiography apparatus or an X-ray fluoroscopic imaging apparatus, and has a console 30 and an imaging apparatus 40. The console 30 of the X-ray apparatus 20 is installed in the control room adjacent to the treatment room. The imaging apparatus 40 of the X-ray apparatus 20 is installed in the treatment room.

The planning apparatus 10 is a medical apparatus connected to the console 30 of the X-ray apparatus 20 so as to be able to communicate with each other via a network such as a local area network (LAN) of the hospital backbone. The planning apparatus 10 includes control circuitry 11, a main memory 12, an input interface 13, a display 14, a cumulative dose distribution data base (DB) 15 and the like.

The control circuitry 11 means any one of dedicated or general central processing unit (CPU) and a micro processor unit (MPU), an application specific integrated circuit (ASIC), and a programmable logic device. The programmable logic device may be, for example, any one of a simple programmable logic device (SPLD), a complex programmable logic device (CPLD), a field programmable gate array (FPGA) and the like. The control circuitry 11 reads programs stored in the main memory 12 or directly implemented in the control circuitry 11 and executes these programs to thereby achieve the following functions.

The control circuitry 11 may be a single circuit or a combination of separate circuits. In the latter case, the main memory 12, which stores the programs, may be separately provided for each of the circuits. Alternatively, a single main memory 12 may store the programs corresponding to the functions of the multiple circuits.

The main memory 12 is constituted by a semiconductor memory element such as a random access memory (RAM), a flash memory, a hard disk, an optical disk, and the like. The main memory 12 may be constituted by a portable medium such as a universal serial bus (USB) memory and a digital video disk (DVD). The main memory 12 stores various processing programs (including an operating system (OS) and the like besides the application program) used in the control circuitry 11 and data necessary for executing the programs. In addition, the OS may include a graphical user interface (GUI) that allows graphics to be used to display information on the display 14 corresponding to the operator and a basic operation can be performed by the input interface 13.

The input interface 13 includes an input device operable by the operator, and an input circuit for inputting a signal from the input device. The input device includes a pointing device (for example, a mouse), a keyboard, various buttons, and the like. The input circuit generates, when the input device is operated by the operator, an input signal corresponding to the operation, and outputs it to the control circuitry 11. It should be noted that the planning apparatus 10 may include a touch panel in which the input device is integrated with the display 14.

The display 14 is a display device such as a liquid crystal display panel, a plasma display panel, and an organic electro luminescence (EL) panel. The display 14 displays the image data generated under the control of the control circuitry 11.

The cumulative dose distribution DB 15 is a storage configured with the HDD, the memory, or the like. The cumulative dose distribution DB 15 can register data of cumulative dose distribution showing the distribution of patient identification information (patient ID) for identifying a patient such as the patient U, and of the three-dimensional integrated dose (mGy) in the body surface of each patient. In general, the cumulative dose distribution is an integrated value of exposure dose generated by unit patient and unit procedure. In the embodiment, examples of procedures of the treatment accompanied with the X-ray irradiation are treatment of arteriovenous malformation (AVM), carotid artery stenting (CAS), coiling corresponding to unruptured cerebral artery aneurysm, coronary artery percutaneous coronary intervention (PCI), transcatheter aortic valve replacement (TAVR), and transcatheter arterial chemo-embolization (TACE) or the like.

Figure 3:
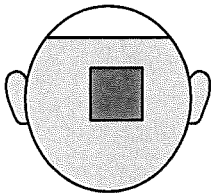
FIG. 3 is a diagram showing an example of the cumulative dose distribution in the X-ray system according to the first embodiment.

FIG. 3 is a diagram showing an example of the cumulative dose distribution in the X-ray system 1.

As shown in FIG. 3, the cumulative dose distribution DB 15 (shown in FIG. 1) can store multiple cumulative dose distributions where cumulative doses in a model coordinate system are associated with respective body surface positions of a three-dimensional human body model. Each cumulative dose distribution is accompanied by the patient identifying information contained in patient information (for example, patients U and V).

FIG. 3 shows the case where mapping of the cumulative doses to the body surface positions of the human body model is stored as the cumulative dose distribution. Alternatively, data on the human body model, and the cumulative doses on the body surface positions may be separately stored. Instead of the human body model, volume data that has already been generated and encompasses the entire patient may be used.

Figure 4:
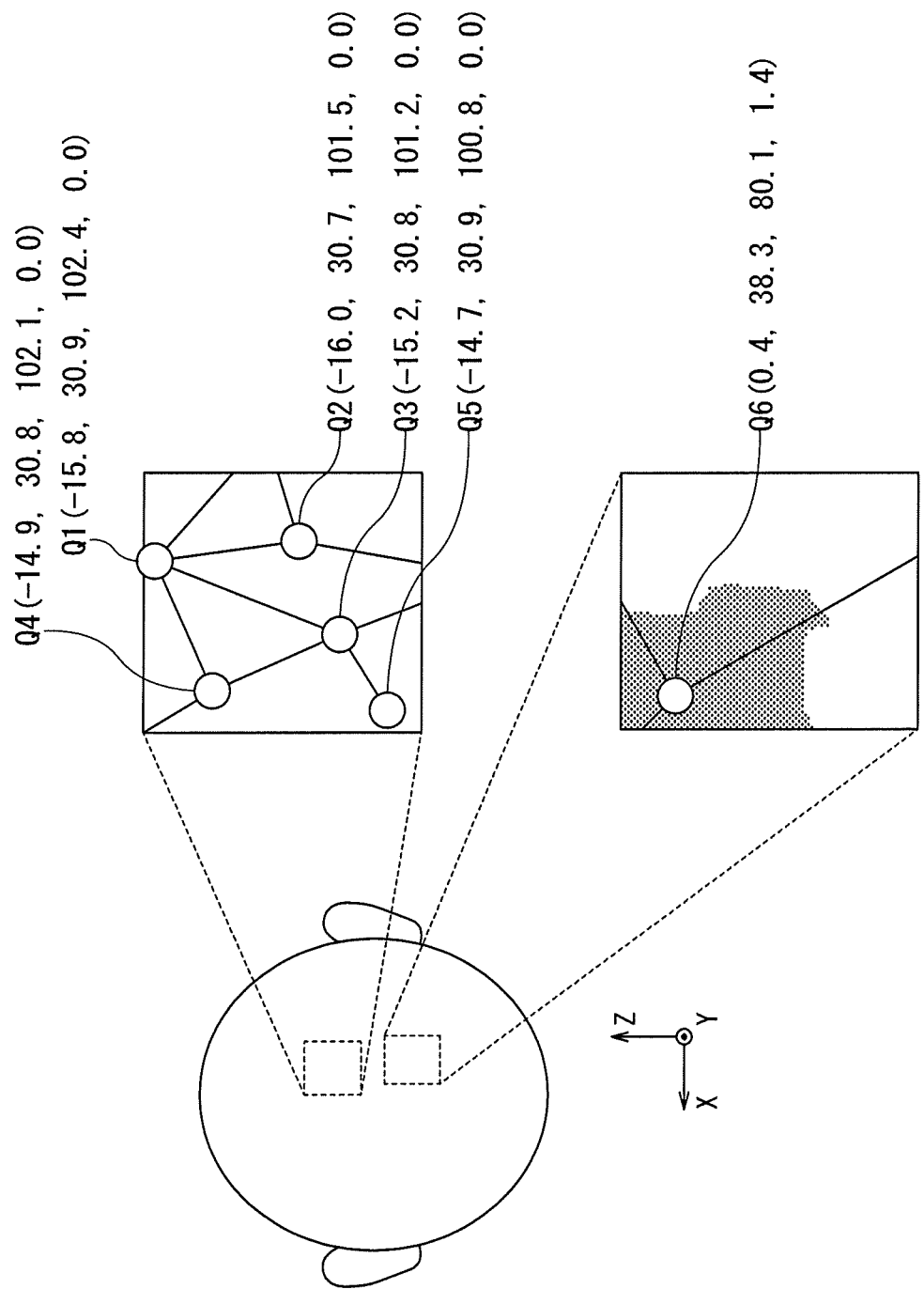
FIG. 4 is a diagram for showing details of the cumulative dose distribution in the X-ray system according to the first embodiment.

FIG. 4 is a diagram for showing details of the cumulative dose distribution in the X-ray system 1.

As shown in FIG. 4, the cumulative dose distribution in the human body model coordinate system is based on the cumulative doses on the body surface positions (points) Q1 to Q6 in the human body model. The body surface positions Q1 to Q6 are associated with information on the X coordinate, Y coordinate, Z coordinate, and cumulative dose (mGy). In the embodiment, the X coordinate corresponds to the lateral direction of the patient. The Y coordinate corresponds to the ventrodorsad direction of the patient. The Z coordinate corresponds to the body axis direction of the patient. The cumulative doses on the body surface positions may be registered separately from or together with the human body model. In the case with no exposure dose (body surface positions Q1 to Q6), the cumulative dose is 0 mGy.

Returning to the explanation of FIGS. 1 and 2, the planning apparatus 10 generates, based on the operations of the control circuitry 11, the main memory 12, the input interface 13, the display 14 and the cumulative dose distribution DB 15, planned data in accordance with indexes "cumulative dose of patient", "visibility of treatment target site" and "exposure dose of surrounding person". The planning apparatus 10 generates the planned data based on data such as volume data generated by imaging the patient and on operation input by the operator (hereinafter referred to as "planner") of the planning apparatus 10. The volume data used in the planning apparatus 10 is data generated in advance by an imaging apparatus (not shown) that can visualize the internal structure of the patient. The volume data is an aggregate of voxels arranged in a three-dimensional direction.

For example, the imaging apparatus includes an X-ray diagnostic apparatus, an X-ray computed tomography (CT) apparatus, a magnetic resonance imaging (MRI) apparatus, a positron emission tomography (PET) apparatus, a single photon emission computed tomography (SPECT) and the like.

The console 30 of the X-ray apparatus 20 is a medical apparatus connected to the planning apparatus 10 via a network such as the LAN of the hospital backbone so as to be mutually communicable. The console 30 includes a control circuitry 31, a main memory 32, an input interface 33, a display 34, an image generating circuit 35, an image processing circuit 36, an image memory 37 and the like, and controls the operation of the imaging apparatus 40.

Since the control circuitry 31, the main memory 32, the input interface 33, and the display 34 of the console 30 have the same configuration as the control circuitry 11, the main memory 12, the input interface 13, and the display 14 of the planning apparatus 10, descriptions thereof will be omitted. The image generating circuit 35 performs, under the control of the control circuitry 31, logarithmic transformation processing (LOG processing) on the projection data output from the imaging apparatus 40, performs addition processing as necessary, thereby generating X-ray image data. The image processing circuit 36 performs, under the control of the control circuitry 31, image processing on the X-ray image data generated by the image generating circuit 35. For example, the image processing includes enlargement/gradation/spatial filter processing corresponding to the data, minimum value/maximum value tracing processing of the data accumulated in time series, addition processing for removing noise, and the like.

The image memory 37 is a storage constituted by a semiconductor memory element such as the RAM, the flash memory or the like, the hard disk, the optical disk, or the like. The image memory 37 stores, under the control of the control circuitry 31, the X-ray image data after image processing by the image processing circuit 36.

The imaging apparatus 40 of the X-ray apparatus 20 is connected to the console apparatus 30, and is a medical apparatus capable of performing X-ray imaging by performing the X-ray irradiation on the patient U. The imaging apparatus 40 is provided with an imaging controller 41, an input interface 43, a display 44, an X-ray irradiator 45, an X-ray detector 46, a C-arm 47 (shown in FIG. 2), a high voltage power supply 48 and a bed 49. In the embodiment, the X-ray imaging includes imaging in which X-rays are irradiated continuously or intermittently (pulse), so-called "fluoroscopy", and one shot of the X-ray irradiation, so-called "radiography". The imaging apparatus 40 may be any device as long as it can perform X-ray imaging, in the case of being an angio system, the case of being an X-ray TV system, and the like. FIGS. 1 and 2 show a case where the imaging apparatus 40 is of an under-tube type. However, it may be an over-tube type.

The input circuit 43 and the display 44 of the imaging apparatus 40 have the same configurations as the input interface 13 and the display 14 of the planning apparatus 10, respectively, and the descriptions thereof will be omitted. The display 44 can display the X-ray image data generated by the console 30 by X-ray imaging as an X-ray image. In a treatment accompanying the X-ray irradiation, the practitioner D such as a doctor can proceed with the treatment while viewing the X-ray image displayed on the display 44 in substantially real time.

The imaging controller 41 includes a control circuitry and a main memory (not shown). The control circuitry and the main memory have the same configurations as the control circuitry 11 and the main memory 12 of the planning apparatus 10, respectively, and the descriptions thereof will be omitted. The imaging controller 41 controls, under the control of the console 30, operations of the X-ray irradiator 45, the X-ray detector 46, the C-arm 47, the high voltage power supply 48, and the bed 49 for X-ray imaging.

The X-ray irradiator 45 is provided at one end of the C-arm 47. Under the control of the imaging controller 41, so that movement in a direction of changing a source image receiving distance (SID), that is, forward and backward movement is possible. The X-ray irradiator 45 is provided with an X-ray source (for example, an X-ray tube) and a movable diaphragm, as not shown in drawings. The X-ray tube receives high voltage power from the high voltage power supply 48, and generates X-rays according to the condition of high voltage power. The movable diaphragm movably supports a diaphragm blade (also called "leaf") constituted by a material which shields X-rays at the X-ray irradiation port of the X-ray tube. A linear quality adjustment filter (not shown) for adjusting the quality of X-rays generated by the X-ray tube may be provided on the front of the X-ray tube.

The X-ray detector 46 is provided at one end of the C-arm 47 so as to face the X-ray irradiator 45. The X-ray detector 46 is provided so as to be able to move back and forth under the control of the imaging controller 41. The X-ray detector 46 includes a flat panel detector (FPD) and an analog to digital (A/D) conversion circuit, as not shown in drawings.

The FPD has detecting elements arranged two-dimensionally. Between each detecting element of the FPD, the scanning line and the signal line are disposed so as to be orthogonal to each other. A grid (not shown) may be provided on the front face of the FPD. In order to absorb the scattered ray incident on the FPD and improve the contrast of the X-ray image, the grid is formed by alternately arranging a grid plate formed of lead or the like having a large X-ray absorption and a grid plate formed of aluminum, wood or the like which is easy to transmit X-rays. The A/D conversion circuit converts the projection data of the time-series analog signal (video signal) output from the FPD into a digital signal, and outputs it to the console 30 via the imaging controller 41.

Incidentally, the X-ray detector 46 may be an image intensifier (I. I.)-TV system. The I. I.-TV system converts the X-rays transmitted through a subject, for example, patient U, and directly incident X-rays into visible light, thereby doubling the luminance in the process of light-electron-light conversion to generate projection data with high sensitivity. Then, the I. I.-TV system converts optical projection data to electric signals using a charge coupled device (CCD) imaging device, and converts the projection data of time series analog signals (video signals) into digital signals.

The C-arm 47 is supported on the ceiling or the floor so as to be rotatable in the left-right direction and the head-foot direction under predetermined restriction with respect to each of the XYZ directions orthogonal to each other. Therefore, it is possible for the C-arm 47 to freely change the X-ray irradiating direction corresponding to the treatment target site of the patient U. In the embodiment, a straight line passing through the center of the detection surface of the X-ray detector from the X-ray focal point of the X-ray tube is defined as an X-ray irradiating direction (also called "working angle") AG (shown in FIG. 2). The X-ray irradiating direction AG is determined by (1) a rotation angle of the C-arm 47, that is, a rotation angle by a rotation in a left-right direction and (2) a rotation angle by a rotation in a cranial direction. The rotation angle of the C-arm 47 in the left-right direction is determined by RAO (Right Anterior Oblique) and LAO (Left Anterior Oblique), and the rotation angle of the C-arm 47 in the cranial direction is CRA (Cranial) and CAU (Caudal).

The high voltage power supply 48 is, under the control of the imaging controller 41, capable of supplying high voltage power to the X-ray tube of the X-ray irradiator 45. The bed 49 is supported on the floor surface and supports the table 491. The bed 49 can perform sliding (move in the X axis, Y axis and Z axis directions) or rolling movement with respect to the table 491 under the control of the imaging controller 41. The table 491 is capable of placing the patient U thereon.

Figure 5:
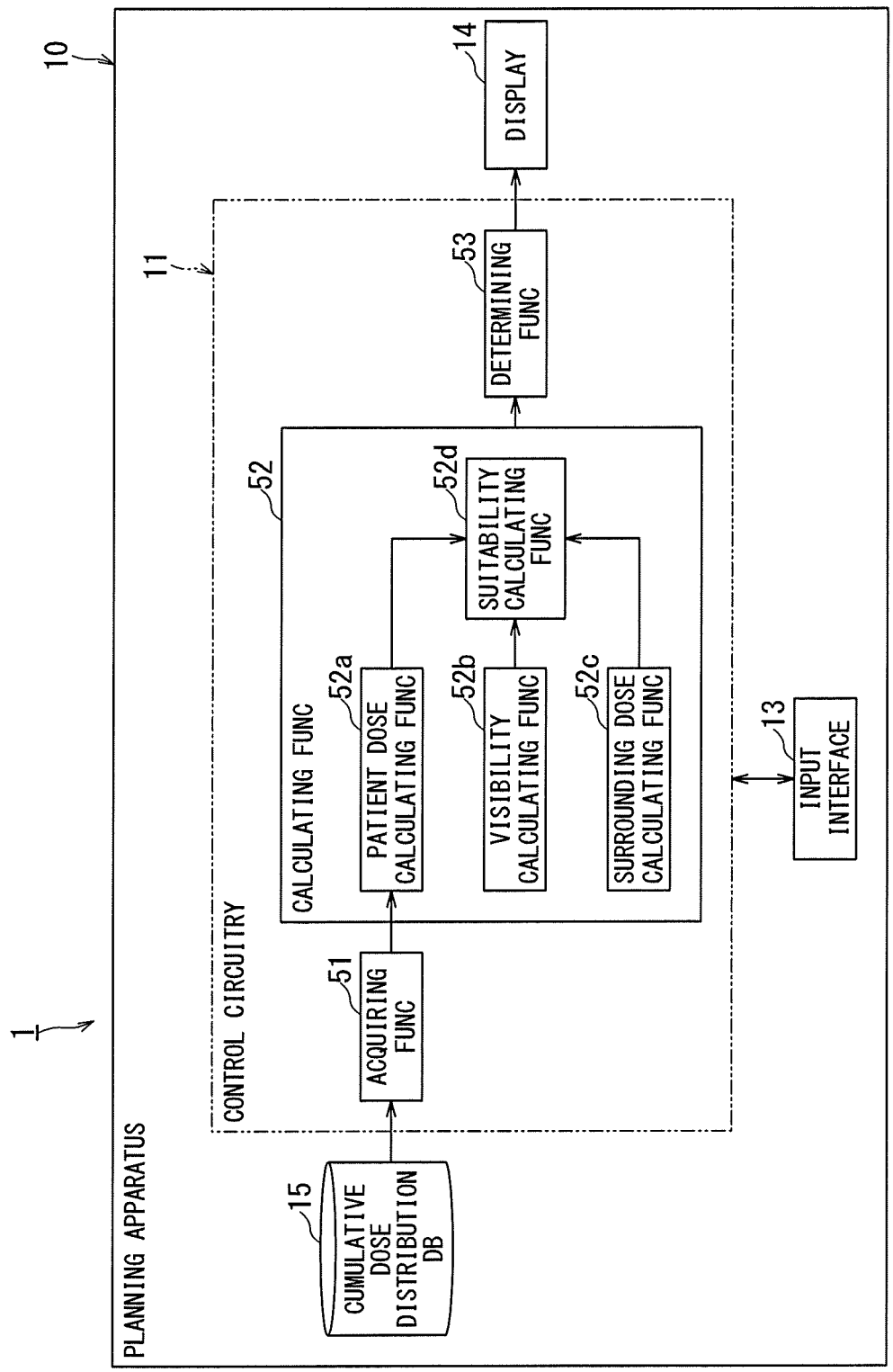
FIG. 5 is a block diagram showing functions of the X-ray system according to the first embodiment.

FIG. 5 is a block diagram showing functions of the X-ray system 1.

The control circuitry 11 of the planning apparatus 10 executes a program, thereby achieving an acquiring function 51, a calculating function 52 and a determining function 53. The description is made assuming that the functions 51 to 53 function as software. Alternatively, all or some of the functions 51 to 53 may be implemented as hardware such as the ASIC in the planning apparatus 10.

The acquiring function 51 includes a function of acquiring a three-dimensional cumulative dose distribution (shown in FIG. 3, hereinafter simply referred to as "cumulative dose distribution") of the patient U from the cumulative dose distribution DB 15.

The calculating function 52 includes a function of calculating multiple rotation angles of the C-arm 47, that is, multiple working angles corresponding to multiple X-ray irradiating directions, as quantitative values. The calculating function 52 has a patient dose calculating function 52a, a visibility calculating function 52b, a surrounding dose calculating function 52c and a suitability calculating function 52d.

The patient dose calculating function 52a includes a function of calculating, based on the cumulative dose distribution acquired by the acquiring function 51, a suitability level corresponding to each X-ray irradiating direction, as a primary suitability level with respect to the index "cumulative dose of patient". That is, based on the cumulative dose distribution, the patient dose calculating function 52a calculates a level of k (k=2, 3, . . . ) levels, the level corresponding to the cumulative dose of the patient U in each X-ray irradiating direction. The method for calculating the primary suitability level of the index "cumulative dose of patient" will be described later with reference to FIGS. 13A, 13B, 14A and 14B.

The visibility calculating function 52b has a function of setting a treatment target site by treatment accompanied with the X-ray irradiation to the patient U, and a function of calculating a suitability level corresponding to each X-ray irradiating direction as a primary suitability level with respect to the index "visibility of treatment target site". That is, the visibility calculating function 52b calculates a level of m (m=2, 3, . . . ) levels, the level corresponding to a size of the treatment target site when viewed in each X-ray irradiating direction. The index "visibility of treatment target site" means the visibility of the treatment target site in the X-ray image, and is quantified based on not only the structure of the treatment target site but also the content of the procedure when treating the treatment target site (during the treatment etc.). The method for calculating the primary suitability level of the index "visibility of treatment target site" will be described later with reference to FIG. 15.

The surrounding dose calculating function 52c includes a function of calculating a suitability level corresponding to each X-ray irradiating direction, as a primary suitability level with respect to the index "exposure dose of surrounding person". That is, the surrounding dose calculating function 52c calculates a level of n (n=2, 3, . . . ) levels, the level corresponding to the exposure dose of the surrounding person in each X-ray irradiating direction. The method for calculating the primary suitability level of the index "exposure dose of surrounding person" will be described later with reference to FIGS. 16A and 16B.

In the embodiment, the surrounding person means a person to be stayed in the treatment room in the treatment accompanying the X-ray irradiation of the patient U. For instance, the surrounding person includes at least one of the practitioner D (shown in FIG. 2) such as a doctor performing the treatment, an operator S (shown in FIG. 2) for performing a rotating operation or the like of the C-arm 47 during the treatment, and a nurse N (shown in FIG. 2) for supporting the treatment.

The suitability calculating function 52d includes a function of calculating, based on at least one of the primary suitability levels of the index "cumulative dose of patient", the index "visibility of treatment target site" and the index "exposure dose of surrounding person", a secondary suitability level of overall indexes, corresponding to each X-ray irradiating direction. The primary suitability level of the index "cumulative dose of patient" corresponds to each X-ray irradiating direction calculated by the patient dose calculating function 52a. The primary suitability level of the index "visibility of treatment target site" corresponds to each X-ray irradiating direction calculated by the visibility calculating function 52b. The primary suitability level of the index "exposure dose of surrounding person" corresponds to each X-ray irradiating direction calculated by the surrounding dose calculating function 52c.

The determining function 53 has a function of determining an X-ray irradiating direction for performing the X-ray irradiation, based on the three-dimensional cumulative dose distribution acquired by the acquiring function 51 and at least the treatment target site set by the visibility calculating function 52b. Specifically, the determining function 53 provides each X-ray irradiating direction and a suitability level (primary or secondary suitability level) corresponding to each X-ray irradiating direction, the suitability level being calculated by the calculating function 52. Therefore, it is possible for the planner to select the X-ray irradiating direction corresponding to the predetermined suitability level from the multiple suitability levels provided, for example, displayed. Then, the determining function 53 determines the selected X-ray irradiating direction as an appropriate X-ray irradiating direction for the X-ray irradiation. Planed data is generated according to the determined X-ray irradiating direction.

Details of the functions 51 to 53 will be described with reference to FIGS. 6 to 16B.

Figure 6:
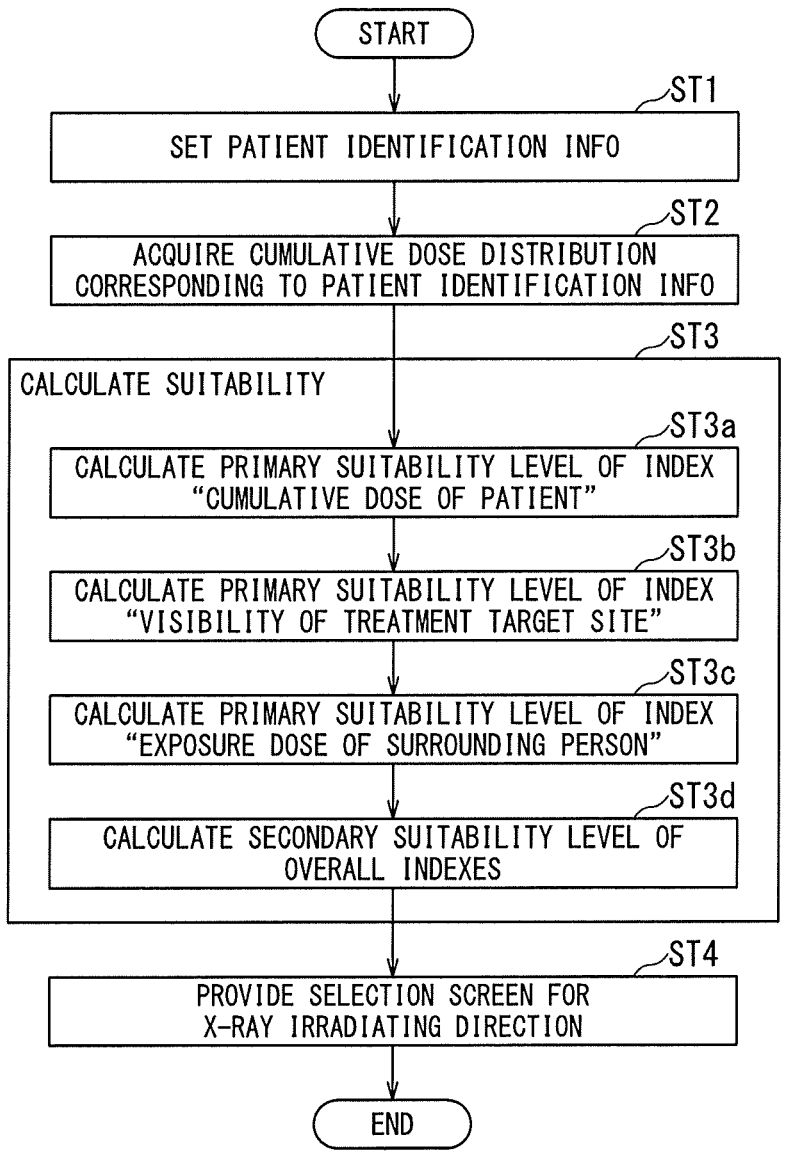
FIG. 6 is a flowchart showing an operation of the X-ray system according to the first embodiment.

FIG. 6 is a flowchart showing an operation of the X-ray system 1. In FIG. 6, a case where the secondary suitability level of overall indexes is calculated and provided, based on the primary suitability level of the index "cumulative dose of patient", the primary suitability level of the index "visibility of treatment target site", and the primary suitability level of the index "exposure dose of surrounding person", will be described. However, it is not limited to that case. The primary suitability level of any one of the three indexes may be provided. Alternatively, the secondary suitability level of overall indexes may be calculated and provided based on the primary suitability level of any two of the three indexes.

The acquiring function 51 of the planning apparatus 10 sets patient identification information (for example, a patient ID) relating to the patient U to be treated, based on the operation of the planner through the input interface 13 (step ST1).

The acquiring function 51 acquires a past cumulative dose distribution corresponding to the patient identification information set in step ST1, out of the cumulative dose distribution DB 15 (step ST2). The acquisition function 51 acquires, when the period condition is set in step ST2, the cumulative dose distribution corresponding to the set patient identification information and corresponding to the range of the period condition, out of the cumulative dose distribution DB 15.

The calculating function 52 calculates multiple suitability levels corresponding to multiple rotation angles of the C-arm 47, that is, multiple X-ray irradiating directions, as quantitative values (step ST3). Specifically, the patient dose calculating function 52*a* of the calculating function 52 calculates a primary suitability level (shown in FIG. 7) of the index "cumulative dose of patient" corresponding to each X-ray irradiating direction, based on the cumulative dose distribution acquired in step ST2 (step ST3*a*). When multiple cumulative dose distributions corresponding to the patient identification information are acquired, the patient dose calculating function 52*a* integrates the multiple cumulative dose distributions, thereby calculating the primary suitability level of the index "cumulative dose of patient". In addition, the visibility calculating function 52*b* calculates a primary suitability level (shown in FIG. 7) of the index "visibility of treatment target site" corresponding to each X-ray irradiating direction (step ST3*b*). The surrounding dose calculating function 52*c* calculates a primary suitability (shown in FIG. 7) of the index "exposure dose of surrounding person" corresponding to each X-ray irradiating direction (step ST3*c*).

FIG. 7 is a table showing the primary suitability level of each index corresponding to each X-ray irradiating direction in the X-ray system 1.

As shown in FIG. 7, multiple X-ray irradiating directions are associated with the index "cumulative dose of patient". That is, a combination of the rotation angle in the left-right direction and the rotation angle in the cranial direction of the C-arm 47 are associated with the index "cumulative dose of patient". In FIG. 7, the rotation angle is set at an interval of 5°, but it is not limited to that case.

The primary suitability level (Score/10 points) is given to the multiple combinations of the rotation angle in the left-right direction and the rotation angle in the cranial direction of the C-arm 47. The primary suitability level "9" points of the index "cumulative dose of patient" may be normalized to be the primary suitability level "0.9". The case of the indexes "visibility of treatment target site" and "exposure dose of surrounding person" is also the same as the index "cumulative dose of patient", so the explanations thereof are omitted.

Returning to the explanation of FIG. 6, the suitability calculating function 52*d* calculate, based on the primary suitability levels of the index "cumulative dose of patient", the index "visibility of treatment target site" and the index "exposure dose of surrounding person", a secondary suitability level of overall indexes, corresponding to each X-ray irradiating direction (step ST3*d*). The primary suitability level of the index "cumulative dose of patient" corresponds to each X-ray irradiating direction calculated in step ST3*a*. The primary suitability level of the index "visibility of treatment target site" corresponds to each X-ray irradiating direction calculated in step ST3*b*. The primary suitability level of the index "exposure dose of surrounding person" corresponds to each X-ray irradiating direction calculated in step ST3*c*.

FIG. 8 is a table showing the secondary suitability level of overall indexes corresponding to each X-ray irradiating direction in the X-ray system 1.

FIG. 8 shows the secondary suitability level (score/30 points) of overall indexes acquired by simply adding the three primary suitability levels corresponding to the three indexes for the same X-ray irradiating direction in the table shown in FIG. 7. For instance, with respect to the rotation angle of −180° in the left-right direction and the rotation angle of −180° in the cranial direction, the primary suitability level "9" points (shown in FIG. 7) of the index "cumulative dose of patient", the primary suitability level "6" points (shown in FIG. 7) of the index "visibility of treatment target site" and the primary suitability level "7" points (shown in FIG. 7) of the index "exposure dose of surrounding person" are simply added, thereby calculating the secondary suitability level "22" points of overall indexes. It should be noted that FIG. 8 shows an example in which the three primary suitability levels are simply added, but the three primary suitability levels may be weighted and added. The secondary suitability level of "22" points of overall indexes may be normalized to the secondary suitability level of "0.73".

Returning to the explanation of FIG. 6, the determining function 53 provides a selection screen of the X-ray irradiating direction to the planner, based on the secondary suitability level of overall indexes corresponding to each X-ray irradiating direction calculated in step ST3*d* (step ST4).

As a first example of the X-ray irradiating direction selection screen, the determining function 53 displays, on the display 14, a table showing the primary suitability level of FIG. 7. When the planner selects a relatively large primary suitability level, based on the table showing the primary suitability level, the X-ray irradiating direction corresponding to the primary suitability level is selected as an appropriate X-ray irradiating direction. Alternatively, as the second example of the X-ray irradiating direction selection screen, the determining function 53 displays, on the display 14, the table showing the secondary suitability level of FIG. 8. When the planner selects a relatively large secondary suitability level, based on the table showing the secondary suitability level, the X-ray irradiating direction corresponding to the secondary suitability level is selected as an appropriate X-ray irradiating direction. Thus, in the determining function 53, it is possible to determine an appropriate X-ray irradiating direction for the X-ray irradiation.

Alternatively, as a third example of the X-ray irradiating direction selection screen, the determining function 53 may display, on the display 14, a distribution showing the primary suitability level in FIGS. 9A to 9C described later. Alternatively, as a fourth example of the X-ray irradiating direction selection screen, the determining function 53 may display, on the display 14, a distribution showing the secondary suitability level in FIG. 10 described later. Alternatively, as a fifth example of the selection screen of the X-ray irradiating direction, the determining function 53 may display, on the display 14, the primary suitability level of FIG. 11 described later, together with the three-dimensional image. Alternatively, as a sixth example of the selection screen of the X-ray irradiating direction, the determining function 53 may display, on the display 14, the secondary suitability level of FIG. 12 described later, together with the three-dimensional image. The display examples shown in FIGS. 9A to 12 will be described below in order.

Figure 9A:
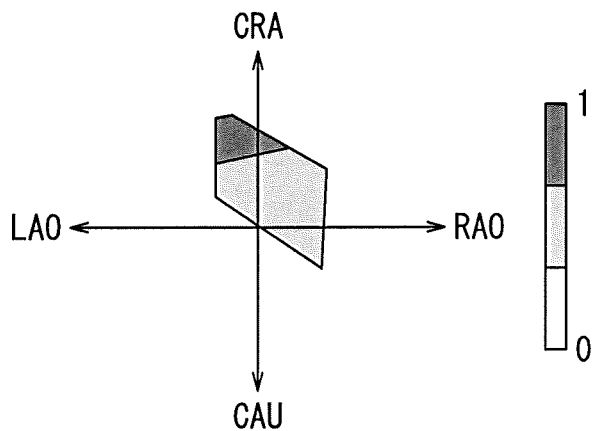
FIGS. 9A to 9C are diagrams showing a third example of an X-ray irradiating direction selection screen in the X-ray system according to the first embodiment.
Figure 9B:
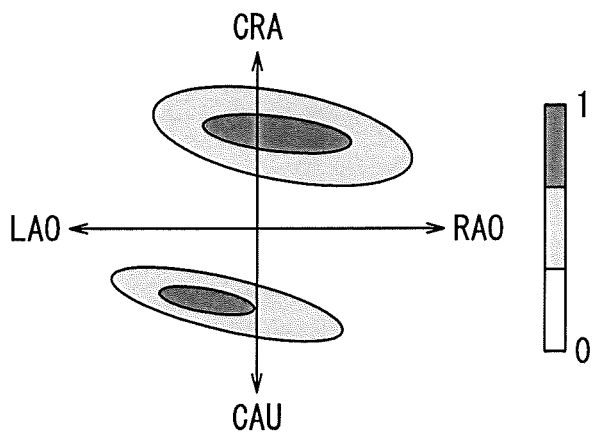
Figure 9C:
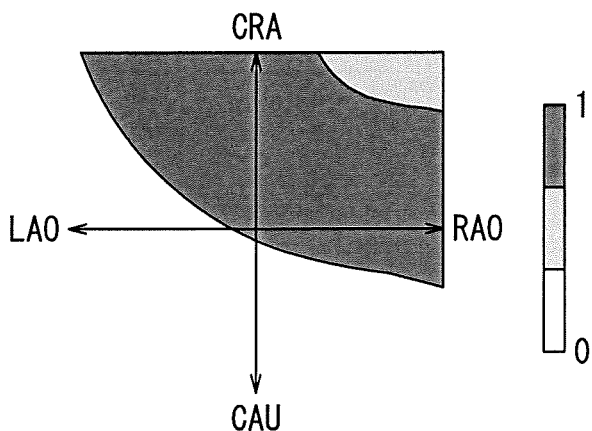

FIGS. 9A to 9C are diagrams showing a third example of the X-ray irradiating direction selection screen in the X-ray system 1. FIG. 9A shows a distribution (first distribution) indicating the primary suitability levels of the index "cumulative dose of patient" for multiple X-ray irradiating directions. FIG. 9B shows a distribution (second distribution) indicating the primary suitability levels of the index "visibility of treatment target site" for multiple X-ray irradiating directions. FIG. 9C shows a distribution (third distribution) indicating the primary suitability levels of the index "exposure dose of surrounding person" for multiple X-ray irradiating directions.

The horizontal axes in FIGS. 9A to 9C indicate the rotation angle in the left-right direction of the C-arm 47, and the vertical axes in FIGS. 9A to 9C indicate the rotation angle in the cranial direction of the C-arm 47. In FIG. 9A, a color according to the primary suitability level (for example, after normalization) of the index "cumulative dose of patient" in the table shown in FIG. 7 is allocated on the coordinate indicating the X-ray irradiating direction. In the case where there is no corresponding primary suitability on the coordinate indicating the X-ray irradiating direction, interpolation may be performed based on the surrounding primary suitability levels.

When the planner selects an area of a relatively large primary suitability level by viewing the distribution based on the index "cumulative dose of patient" shown in FIG. 9A, the determining function 53 determines an X-ray irradiating direction corresponding to the selected area as an appropriate X-ray irradiating direction. Alternatively, the determining function 53 may determine, as an appropriate X-ray irradiating direction, a direction in which the cumulative dose is equal to or less than a predetermined threshold value at any position of the cumulative dose distribution.

The index "visibility of treatment target site" shown FIG. 9B and the index "exposure dose of surrounding person" shown in FIG. 9C are the same as those in the case of the index "cumulative dose of patient" shown in FIG. 9A, so the explanations thereof are omitted.

Figure 10:
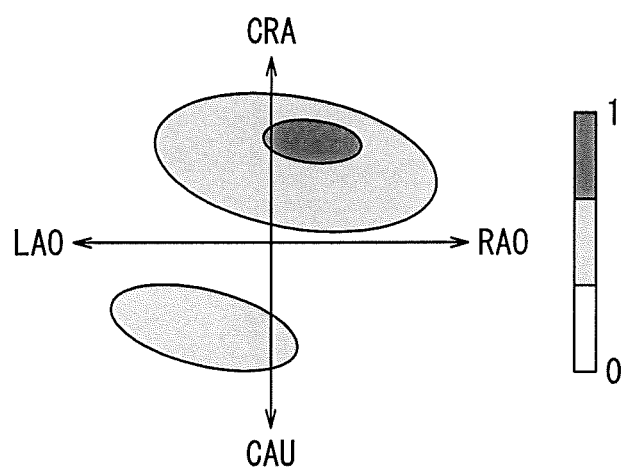
FIG. 10 is a diagram showing a fourth example of an X-ray irradiating direction selection screen in the X-ray system according to the first embodiment.

FIG. 10 is a diagram showing a fourth example of the X-ray irradiating direction selection screen in the X-ray system 1. FIG. 10 shows a distribution indicating the secondary suitability level of the three indexes for the multiple X-ray irradiating directions.

In FIG. 10, the horizontal axis indicates the rotation angle in the left-right direction of the C-arm 47, and the vertical axis indicates the rotation angle in the cranial direction of the C-arm 47. In FIG. 10, a color according to the level of secondary suitability (for example, after normalization) in the table shown in FIG. 8 is allocated on the coordinate indicating the X-ray irradiating direction. In the case where there is no corresponding secondary suitability on the coordinate indicating the X-ray irradiating direction, interpolation may be performed based on the surrounding secondary suitability levels.

When the planner selects an area of a relatively large secondary suitability level by viewing the distribution based on the three indexes shown in FIG. 10, the determining function 53 determines an X-ray irradiating direction corresponding to the selected area as an appropriate X-ray irradiating direction.

Figure 11:
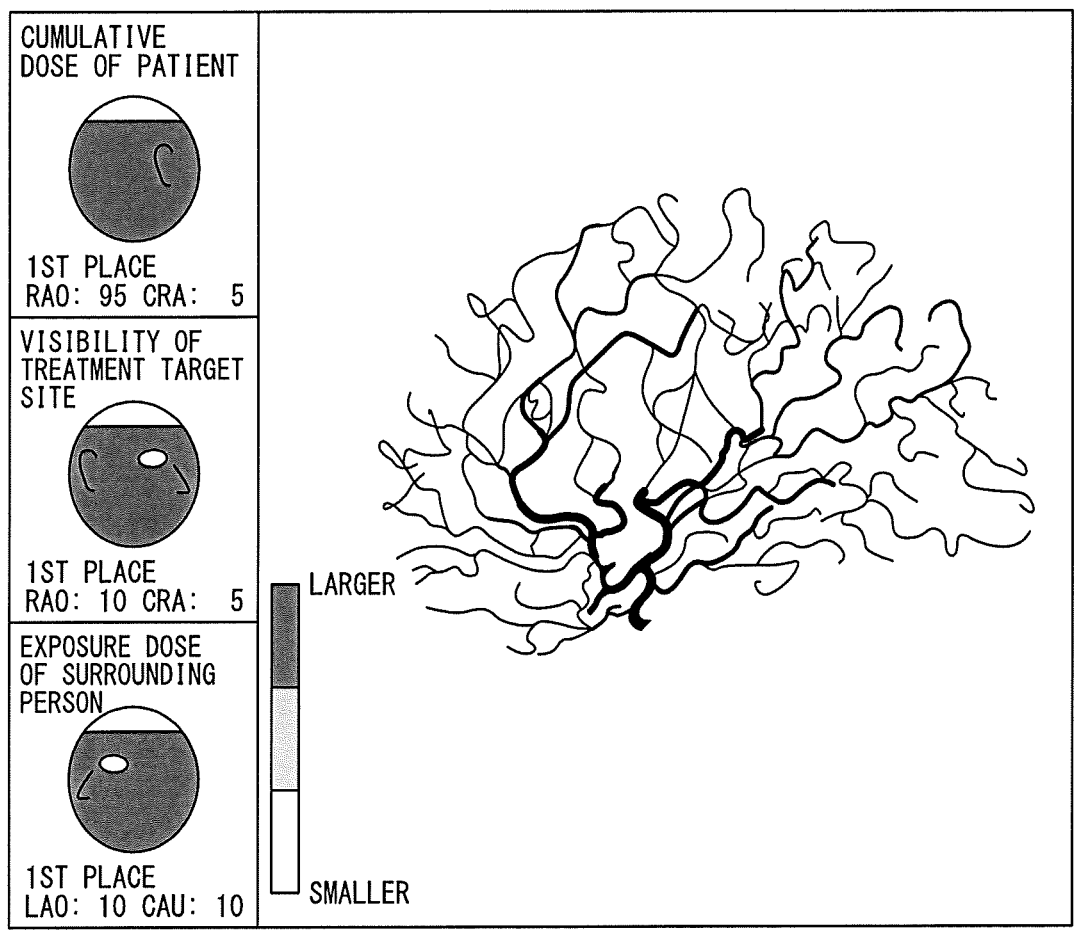
FIG. 11 is a diagram showing a fifth example of the X-ray irradiating direction selection screen in the X-ray system according to the first embodiment.

FIG. 11 is a diagram showing a fifth example of the X-ray irradiating direction selection screen in the X-ray system 1. FIG. 11 shows the primary suitability level of each index with the three-dimensional image. In FIG. 11, for each index, the first place (or maximum) of the primary suitability level and the corresponding X-ray irradiating direction are displayed on the display 14.

The upper row on the left side of FIG. 11 shows an X-ray irradiating direction corresponding to the first place of the primary suitability level of the index "cumulative dose of patient" in the table shown in FIG. 7, and a three-dimensional image when the cumulative dose distribution which is the three-dimensional model is viewed from the X-ray irradiating direction. Similarly, the middle row on the left side of FIG. 11 shows an X-ray irradiating direction corresponding to the first place of the primary suitability level of the index "visibility of treatment target site" in the table shown in FIG. 7, and a three-dimensional image thereof. Similarly, the lower row on the left side of FIG. 11 shows an X-ray irradiating direction corresponding to the first place of the primary suitability level of the index "exposure dose surrounding person" in the table shown in FIG. 7, and a three-dimensional image thereof. It should be noted that a comparison may be made between the multiple primary suitability levels corresponding to the multiple X-ray irradiating directions at regular intervals (for example, 10° intervals).

The right side of FIG. 11 shows a three-dimensional image. This three-dimensional image corresponds to the three-dimensional image (for example, an upper three-dimensional image on the left side) selected by the planner out of the three three-dimensional images on the left side, the three-dimensional image being acquired by rendering the volume data used at the treatment planning, in the X-ray irradiating direction of the selected three-dimensional image. Thus, if the X-ray imaging is performed in the X-ray irradiating direction of the three-dimensional image selected on the left side, it is possible to predict what kind of the X-ray image will be displayed in the future treatment using the image on the right side. It should be noted that it is possible to three-dimensionally rotate the three-dimensional image of the model (that is, rotate in the X-ray irradiating direction) selected, by the planner, out of the three three-dimensional images on the left side. Following this rotation, the display of the right three-dimensional image is also rotated.

While viewing the right three-dimensional image based on the primary suitability level selected on the left side of FIG. 11, it is possible for the planner to select an X-ray irradiating direction which is expected to be easy to observe in the treatment, as an appropriate X-ray irradiating direction.

Figure 12:
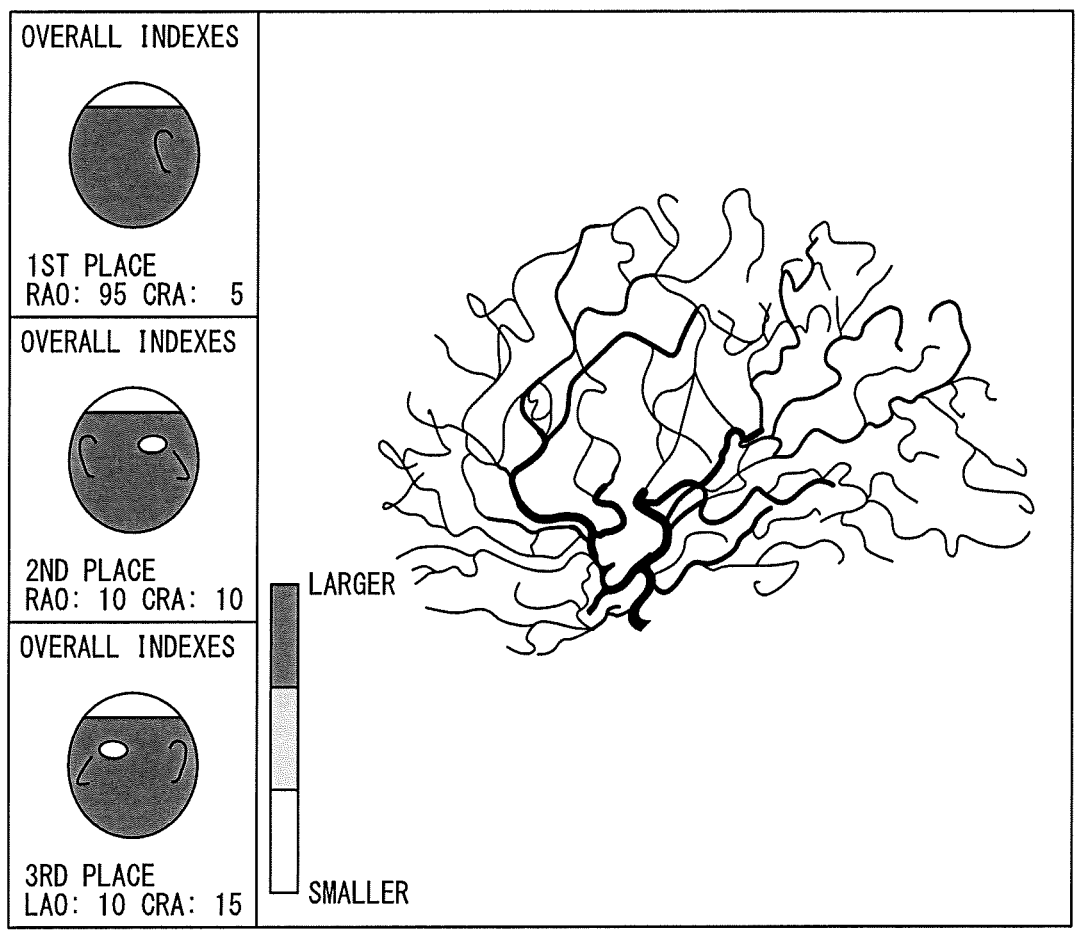
FIG. 12 is a diagram showing a sixth example of the X-ray irradiating direction selection screen in the X-ray system according to the first embodiment.

FIG. 12 is a diagram showing a sixth example of the X-ray irradiating direction selection screen in the X-ray system 1. FIG. 12 shows the secondary suitability level of overall indexes with the three-dimensional image. In FIG. 12, the secondary suitability levels corresponding to each X-ray irradiating direction are displayed on the display 14 in the order of secondary suitability level order.

The upper row on the left side of FIG. 12 shows the X-ray irradiating direction corresponding to the first place of the secondary suitability level in the table shown in FIG. 8, and a three-dimensional image when the cumulative dose distribution which is the three-dimensional model is viewed from the X-ray irradiating direction. Similarly, the middle row on the left side of FIG. 12 shows the X-ray irradiating direction corresponding to the second place of the secondary suitability level in the table shown in FIG. 8 and a three-dimensional image thereof. Similarly, the lower row on the left side of FIG. 12 shows the X-ray irradiating direction corresponding to the third place of the secondary suitability level in the table shown in FIG. 8 and a three-dimensional image thereof. It should be noted that a comparison may be made between the multiple secondary suitability levels corresponding to the multiple X-ray irradiating directions at regular intervals (for example, 10° intervals).

It should be noted that the determining function 53 may provide X-ray irradiating directions in descending order of the secondary suitability levels corresponding to the three indexes when the suitability level of any one of indexes is equal to or more than a threshold value, the index being selected from the index "cumulative dose of patient", the index "visibility of treatment target site", and the index "exposure dose of surrounding person". For example, in the case where the procedure is coiling of a cerebral aneurysm, since the therapeutic effect is emphasized, the determining function 53 provides X-ray irradiating directions in descending order of the secondary suitability levels corresponding to the three indexes when the suitability level (after normalization) of the index "visibility of treatment target site" is 0.8 or more. In addition, for example, in the case where the procedure is PCI, since the operation is extended for a long time, the determining function 53 provides X-ray irradiating directions in descending order of the secondary suitability levels corresponding to the three indexes when the suitability level (after normalization) of the index "cumulative dose of patient" is 0.8 or more. When there is a primary suitability level less than a threshold value of the multiple primary suitability levels corresponding to each X-ray irradiating direction, the determination function 53 may exclude a secondary suitability level corresponding to that primary suitability level from the display in the order of the secondary suitability level order.

The right side of FIG. 12 shows a three-dimensional image. This three-dimensional image corresponds to the three-dimensional image (for example, an upper three-dimensional image on the left side) selected by the planner out of the three three-dimensional images on the left side, the three-dimensional image being acquired by rendering the volume data used at the treatment planning, in the X-ray irradiating direction of the selected three-dimensional image. Thus, if the X-ray imaging is performed in the X-ray irradiating direction of the three-dimensional image selected on the left side, it is possible to predict what kind of the X-ray image will be displayed in the future treatment using the image on the right side. It should be noted that it is possible to three-dimensionally rotate the three-dimensional image of the model (that is, rotate in the X-ray irradiating direction) selected, by the planner, out of the three three-dimensional images on the left side. Following this rotation, the display of the right three-dimensional image also is rotated.

While viewing the right three-dimensional image based on the secondary suitability level selected on the left side of FIG. 12, it is possible for the planner to select an appropriate X-ray irradiating direction which is expected to be easy to observe in the treatment.

Although examples of display have been described with reference to FIGS. 7 to 12, the present invention is not limited thereto. For instance, the determining function 53 may display, side by side, a dose projection image based on the three-dimensional cumulative dose distribution of the patient U, and a morphological projection image based on the volume data. In this case, in a state in which the dose projection image and the morphological projection image are displayed as different applications and different windows, the display angles, that is, the projection angles are synchronized in the applications, and the projected images are displayed. The determining function 53 may display the dose projection image and the morphological projection image with different screen sizes. In this case, the determining function 53 may limit the display portion of the dose projection image. After the projection angle is changed, the determining function 53 convolutes (synthesizes) the dose projection image and the morphological projection image according to the changed projection angle. With this display method, it is possible for the planner to easily recognize the relationship visually between the dose projection image and the morphological projection image. The cumulative dose distribution may be a cumulative dose of an organ such as a blood vessel, rather than a cumulative dose of the skin.

Subsequently, a method of calculating the primary suitability level of each index will be described.

A. Primary Suitability Level of Index "Cumulative Dose of Patient"

The patient dose calculating function 52a (shown in FIG. 5) calculates the primary suitability level of the index "cumulative dose of patient" in each X-ray irradiating direction, based on the cumulative dose distribution which is the three-dimensional model.

Each of FIGS. 13A and 13B is a diagram for explaining a method of calculating the primary suitability level of the index "cumulative dose of patient" in the X-ray system 1. FIG. 13A is a diagram for explaining an addition method in the case where there are cumulative dose distributions in the past relating to the patient U. The patient dose calculating function 52a calculates a cumulative dose distribution DT by simple addition of past cumulative dose distributions D1 and D2 of the patient U. The patient dose calculating function 52a simply adds corresponding points of each cumulative dose distribution. The patient dose calculating function 52a may weighted add the cumulative dose distributions D1 and D2 in consideration of the attenuation of the dose due to the elapsed time from the examination/treatment time to the present. The patient dose calculating function 52a may weighted add the cumulative dose distributions D1 and D2 by multiplying a highly sensitive portion (for example, crystalline lens or the like) corresponding to X-ray by one or more coefficients.

FIG. 13B is a cross-sectional view showing the cumulative dose distribution in the past relating to the patient U. As shown in FIG. 13B, in the cumulative dose distribution DT, in the X-ray irradiating direction AG1 with respect to the treatment target site M, the X-rays pass through the body surface portion H having a relatively large cumulative dose. As shown in FIG. 13B, in the cumulative dose distribution DT, in the X-ray irradiating direction AG2 for the treatment target site M, the X-rays do not pass through the body surface portion H having a relatively large cumulative dose. Therefore, the patient dose calculating function 52a can calculate, as a quantitative value, the primary suitability level corresponding to the dose at each position on the body surface through which the X-ray irradiating directions AG1, AG2, . . . pass to the treatment target site M. For example, the patient dose calculating function 52a determines, as one of 10 (k=10) levels, the primary suitability level corresponding to the X-ray irradiating direction AG1 according to the dose of the position on the body surface through which the X-ray irradiating direction AG1 passes.

In the embodiment, the patient dose calculating function 52a may set an X-ray irradiating region determined by the size of the FPD of the X-ray detector 46 as a three-dimensional field of view (FOV). Therefore, the patient dose calculating function 52a calculates the suitability level of the cumulative dose of the patient U, using the maximum value (maximum cumulative dose) of the cumulative dose in the three-dimensional FOV. In this case, the patient dose calculating function 52a performs position matching (for example, rigid body alignment) between the cumulative dose distribution of the patient U and the volume data of the patient U, and generates three-dimensional synthetic data.

FIGS. 14A and 14B are diagrams for explaining a method of calculating the primary suitability of the index "cumulative dose of patient" in the X-ray system 1.

As shown in FIG. 14A, the patient dose calculating function 52a acquires the maximum cumulative dose from the three-dimensional FOV included in the three-dimensional synthetic data. The patient dose calculating function 52a can calculate the cumulative dose of the patient by applying the maximum cumulative dose to an equation shown in FIG. 14B. It should be noted that the maximum value (threshold value) of the maximum cumulative dose shown in FIG. 14B may be arbitrarily changed by the planner in consideration of the age and the like of the patient U.

B. Primary Suitability Level of Index "Visibility of Treatment Target Site"

The visibility calculating function 52b (shown in FIG. 5) calculates the primary suitability level of the index "visibility of treatment target site", based on the size of the treatment target site observed from each X-ray irradiating direction.

FIG. 15 is a diagram for explaining a method of calculating the primary suitability level of the index "visibility of treatment target site" in the X-ray system 1.

For instance, as shown in FIG. 15, the visibility calculating function 52b classifies, as a segmentation region, the treatment target site of the volume data of the patient U used at the time of the treatment planning. The visibility calculating function 52b generates projection images of the segmentation region viewed from projecting directions corresponding to the respective X-ray irradiating directions AG3 and AG4, and calculates a primary suitability level, based on the area of the treatment target site on each projection image. Therefore, the visibility calculating function 52b can calculate, as a quantitative value, the primary suitability level corresponding to each area of the treatment target site when the treatment target site M is viewed from the projecting directions corresponding to the respective X-ray irradiating directions AG3 and AG4. For instance, the visibility calculating function 52b determines the primary suitability level corresponding to the X-ray irradiating direction AG3 as one of 10 (m=10) levels according to the area of the treatment target site in the X-ray irradiating direction AG3.

When the area of the treatment target site is calculated based on the projection image and when the tissue other than the treatment target site is present on the near side (viewpoint side) of the treatment target site, the visibility calculating function 52b may convert the region of the tissue as the area of the treatment target site or not. Alternatively, the planning apparatus 10 may preliminarily have stored, as a database, a shape in which the treatment target site is best viewed for each type of procedure. In this case, the visibility calculating function 52b calculates the primary suitability level in each X-ray irradiating direction as one of ten levels, in accordance with the degree of coincidence of the template matching result between the shape of the treatment target site and the segmentation region of the volume data.

C. Primary Suitability Level of Index "Exposure Dose of Surrounding Person"

The surrounding dose calculating function 52c (shown in FIG. 5) calculates the primary suitability level of the index "exposure dose of surrounding person", based on the exposure dose of surrounding people in each X-ray irradiating direction.

Each of FIGS. 16A and 16B is a diagram for explaining a method of calculating the primary suitability level of the index "exposure dose of surrounding person" in the X-ray system 1.

Each of FIGS. 16A and 16B shows the relationship between the table 491 of the bed 49, the X-ray irradiator 45, and the surgeon, for example, the practitioner D such as a doctor, and shows the patient U viewed from the head side of the patient U. The surrounding dose calculating function 52c can calculate, as a quantitative value, the primary suitability level corresponding to the exposure dose of the practitioner D caused by the scattered ray in X-ray irradiating directions. For instance, the surrounding dose calculating function 52c determines, as one of 10 (n=10) levels, the primary suitability level in the X-ray irradiating direction shown in FIG. 16A, in accordance with the exposure dose in the X-ray irradiating directions shown in FIG. 16A.

The surrounding dose calculating function 52c may use a position stored in the main memory 12 in advance, as the standing position of the surrounding person, or may use a position changed dynamically by the planner. The primary suitability level of the index "exposure dose of surrounding person" may take into account the exposure dose of only the practitioner D, or the maximum exposure dose among the practitioner D, the operator S, and the nurse N. It should be noted that a known method may be used as a calculation method of the exposure dose by the scattered ray determined by the X-ray irradiating direction and the standing position of the surrounding people and the like.

In the above description, the planning apparatus 10 as the medical apparatus has the functions 51 to 53, and the planning apparatus 10 provides the selection screen of the appropriate X-ray irradiating direction, but it is not limited to that case. For instance, the console 30 as the medical apparatus that controls the imaging apparatus 40 may have the functions 51 to 53, and the console 30 may be configured to provide the selection screen of the appropriate X-ray irradiating direction.

As described above, according to the X-ray system 1 including the medical apparatus such as the planning apparatus 10, and the medical apparatus, it is possible to quickly determine, in the time of treatment planning, the X-ray irradiating direction at the time of subsequent treatment, so it is possible to realize shortening of the planning time. Further, according to the X-ray system 1 including the medical apparatus such as the planning apparatus 10, and the medical apparatus, for the practitioner D such as a doctor, it is possible to proceed the procedure corresponding to the patient U with the determined appropriate X-ray irradiating direction, so it is possible to shorten the treatment time and improve the treatment effect.

2. Second Embodiment

In the above description, it is described that the appropriate X-ray irradiating direction is provided in the time of treatment planning, but the present invention is not limited to that case. For instance, the console 30 of the X-ray apparatus 20 may be configured to update, in real time (including "approximately real time" in which calculating time is taken into account), the suitability level (first or second suitability level) according to the X-ray irradiating direction during the treatment on the treatment target site of the patient U, that is, during the X-ray radiation. Since a configuration of an X-ray system according to a second embodiment is equivalent to the configuration shown in FIG. 1, description thereof will be omitted. In addition, an appearance of an imaging apparatus provided in the X-ray system according to the second embodiment is equivalent to the appearance shown in FIG. 2, so description thereof will be omitted.

FIG. 17 is a block diagram showing functions of the X-ray system according to the second embodiment.

FIG. 17 shows an X-ray system 1A according to the second embodiment. The X-ray system 1A includes a planning apparatus 10 and an X-ray apparatus 20. The X-ray apparatus 20 is provided with a console 30 and an imaging apparatus 40. In FIG. 17, the same members as those in FIGS. 1 and 2 are denoted by the same reference numerals, and description thereof is omitted.

The control circuitry 31 of the console 30 executes a program, thereby achieving an acquiring function 61, an imaging function 62, a calculating function 63 and a providing function 64. The description is made assuming that the functions 61 to 64 function as software. Alternatively, all or some of the functions 61 to 64 may be implemented as hardware such as the ASIC in the console 30.

The acquiring function 61 includes a function of acquiring the planed data from the planning apparatus 10. The planed data includes suitability levels (primary or secondary suitability level) corresponding to X-ray irradiating directions, and the appropriate X-ray irradiating direction for the patient U selected by the planning apparatus 10.

The imaging function 62 includes a function of setting up the C-arm 47 of the imaging apparatus 40 according to the X-ray irradiating direction acquired by the acquiring function 61. The imaging function 62 includes a function of controlling the imaging apparatus 30 to execute the X-ray irradiation.

The calculating function 63 includes a function of calculating, in real time, the suitability level corresponding to a current X-ray irradiating direction as a quantitative value. The calculating function 63 includes a patient dose calculating function 63a, a visibility calculating function 63b, and a suitability calculating function 63d.

The patient dose calculating function 63a includes a function of acquiring, from the suitability levels corresponding to the X-ray irradiating directions acquired by the acquiring function 61, a past suitability level corresponding to a current X-ray irradiating direction with respect to the index "cumulative dose of patient". The patient dose calculating function 63a includes a function of calculating a cumulative dose corresponding to the current X-ray irradiating direction using the DTS, and calculating, in real time, a current suitability level corresponding to the calculated cumulative dose as a quantitative value. In addition, the patient dose calculating function 63a includes a function of adding, in real time, the current suitability level to the past suitability level.

The visibility calculating function 63b includes a function of calculating, in real time, a primary suitability level corresponding to the current X-ray irradiating direction with respect to the index "visibility of treatment target site". The calculating function 63 may include a function of calculating, in real time, a primary suitability level corresponding to the current X-ray irradiating direction with respect to the index "exposure dose of surrounding person".

The suitability calculating function 63d includes a function of calculating, in real time, based on at least one of the primary suitability levels of the index "cumulative dose of patient" and the index "visibility of treatment target site", a secondary suitability level of overall indexes, corresponding to each X-ray irradiating direction. The primary suitability level of the index "cumulative dose of patient" corresponds to each X-ray irradiating direction calculated by the patient dose calculating function 63a. The primary suitability level of the index "visibility of treatment target site" corresponds to each X-ray irradiating direction calculated by the visibility calculating function 63b.

The providing function 64 includes a function of providing, in real time, the suitability level (primary or secondary suitability level) corresponding to the X-ray irradiating direction during the X-ray irradiation, calculated by the calculating function 63. It is possible for the surrounding person to confirm, in real time, the provided suitability level, for example, the displayed suitability level with respect to the current X-ray irradiating direction.

Details of the functions 61 to 64 will be described with reference to FIGS. 18 to 20D.

The whole of FIGS. 18 and 19 is a flowchart showing an operation of the X-ray system 1A. In FIG. 18, a case where the secondary suitability level of overall indexes is, in real time, calculated and provided, based on the primary suitability level of the index "cumulative dose of patient" and the primary suitability level of the index "visibility of treatment target site", will be described. However, it is not limited to that case. The secondary suitability level of overall indexes may be calculated and provided based on the primary suitability level of any one of the two indexes.

The acquiring function 51 of the planning apparatus 10 sets patient identification information (patient ID) regarding the patient U which is a treatment target and placed on the table 491, based on the operation of the input interface 33 by the surrounding person (step ST11).

The acquiring function 61 acquires planed data, that is, multiple primary suitability level corresponding to multiple X-ray irradiating directions, and an appropriate X-ray irradiating direction relating to the patient U, from the planning apparatus 10, the appropriate X-ray irradiating direction being selected by the planning apparatus 10 (step ST12). The imaging function 62 sets up the C-arm 47 according to the initial X-ray irradiating direction acquired in step ST12 for the patient U corresponding to the patient identification information set in step ST11 (step ST13). The imaging function 62 acquires the past primary suitability level corresponding to the initial X-ray irradiating direction, out of the plurality of primary suitability levels acquired in step ST12 (step ST14). The imaging function 62 starts treatment with the X-ray irradiation (step ST15).

The calculating function 63 calculates, in real time, the suitability level corresponding to the initial X-ray irradiating direction (or the new X-ray irradiating direction acquired in step ST19 of FIG. 19) acquired in step ST14 as a quantitative value (step ST16). Specifically, the patient dose calculating function 63a adds the primary suitability level corresponding to the current X-ray irradiating direction in the X-ray irradiation started in step ST15 to the past primary suitability level corresponding to the initial X-ray irradiating direction acquired in step ST14 with respect to the index "cumulative dose of patient", and calculates, in real time, a primary suitability level corresponding to the current the X-ray irradiation direction (step ST16a). The visibility calculating function 63b calculates, in real time, a primary suitability level corresponding to the current X-ray irradiating direction in the X-ray irradiation started in step ST15 with respect to the index "visibility of treatment target site" (step ST16b). It should be noted that, the primary suitability level of "visibility of treatment target site" does not change, as long as the X-ray irradiating direction is not changed.

The suitability calculating function 63d calculate, in real time, based on the primary suitability levels of the index "cumulative dose of patient" and the index "visibility of treatment target site", a secondary suitability level of overall indexes, corresponding to the current X-ray irradiating direction (step ST16d). The primary suitability level of the index "cumulative dose of patient" corresponds to the current X-ray irradiating direction calculated in step ST16a. The primary suitability level of the index "visibility of treatment target site" corresponds to the current X-ray irradiating direction calculated in step ST16b.

Proceeding to the explanation of FIG. 19, the providing function 64 provides, to the surrounding person, the secondary suitability level of overall indexes corresponding to the current X-ray irradiating direction calculated in step ST16d (step ST17). For instance, the providing function 64 displays, on the display 44, the secondary suitability level of overall indexes corresponding to the current X-ray irradiating direction.

Each of FIGS. 20A to 20D is a diagram showing a display example of the primary suitability level corresponding to the current X-ray irradiating direction in the X-ray system LA. Each of FIGS. 20A to 20D is a diagram showing, as a radar chart, the primary suitability level corresponding to the current X-ray irradiating direction.

FIG. 20A shows the primary suitability level of each index corresponding to the X-ray irradiating direction selected at the treatment planning, that is, just before treatment T1. When the treatment of the treatment target site accompanied with the X-ray irradiation is started, as shown in the treatment T2 in FIG. 20B, the suitability levels of the index "cumulative dose of patient" and the index "exposure dose of surrounding person" decrease, gradually.

Returning to the explanation of FIG. 19, the providing function 64 determines whether or not the rotation angle of the C-arm 47 is maintained (step ST18). If it is determined as "NO" in step ST18, that is, if it is determined that the rotation angle of the C-arm 47 is instructed from the input interface 33, that is, if the providing function 64 determines that the rotation angle of the C-arm 47 is not maintained, the imaging function 62 moves the C-arm 47 in accordance with a new X-ray irradiating direction (step ST19). The imaging function 62 acquires the past primary suitability level corresponding to the new X-ray irradiating direction out of the primary suitability levels acquired in step ST12 (step ST20). Then, the process returns to step ST16 in FIG. 18.

The operation of the C-arm 47 during the rotational movement will be described with reference to FIGS. 20C and 20D. When the X-ray irradiating direction is changed from the treatment time T2 shown in FIG. 20B, the suitability level of the index "visibility of treatment target site" is changed as shown at treatment time T3 in FIG. 20C. After a lapse of time from the treatment time T3, the suitability level of the index "cumulative dose of patient" and the suitability level of the index "exposure dose of surrounding person" decrease gradually, as shown in the treatment time T4 of FIG. 20D. It should be noted that the providing function 64 may issue a warning when any level of suitability falls below the threshold value during the treatment. In addition to the radar chart, the providing function 64 may display the rotation angle of the C-arm 47.

Returning to the explanation of FIG. 19, if it is determined as "YES" in step ST18, that is, if it is determined that the rotation angle of the C-arm 47 is not instructed from the input interface 33, that is, if the providing function 64 determines that the rotation angle of the C-arm 47 is maintained, the imaging function 62 determines whether or not the treatment accompanying the X-ray irradiation started in step ST15 is ended (step ST21). If it is determined as "NO" in step ST21, that is, if it is determined that there is no instruction to instruct the X-ray irradiation from the input interface 33, that is, if it is determined that the treatment accompanied with the X-ray irradiation is not ended, the process returns to step ST16 in FIG. 18.

If it is determined as "YES" in step ST21, that is, if it is determined that there is an instruction to end the X-ray irradiation from the input interface 33, that is, if it is determined that the treatment accompanied with the X-ray irradiation is ended, the console 30 ends the X-ray irradiation.

As described above, according to the X-ray system 1A including the medical apparatus such as the planning apparatus 10, and the medical apparatus, it is possible for the surrounding person to proceed, during the treatment, the procedure while visually recognizing whether the current X-ray irradiating direction is appropriate, so it is possible to shorten the treatment time and improve the treatment effect.

3. Modified Example

In the above description, only three indexes are used, but it is not limited to the above three indexes. For instance, one of the indexes may be "efficiency of treatment". The index "efficiency of treatment" means a distance between a surrounding person and the X-ray irradiator 45 or the X-ray detector 46 held by the C-arm 47, the surrounding person being, for example, the practitioner D such as a doctor, the operator S of the C-arm 47 and the nurse N. The calculating function 52 shown in FIG. 5 (or the calculating function 63 shown in FIG. 17) can calculate the suitability level corresponding to each X-ray irradiating direction, as the primary suitability level for the index "efficiency of treatment". That is, the calculating function 52 calculates an appropriate level, based on the p (p=2, 3, . . . ) levels of the distance in each X-ray irradiating direction. A movement space in which the practitioner D such as a doctor moves, a movement space in which the operator S moves, and a movement space of the nurse N supporting the treatment are registered in advance in the database for each type of procedure.

FIG. 21 is a top view showing a movement space of a surrounding person in a modified example of the X-ray systems 1 and 1A.

FIG. 21 is a view showing a three-dimensional movement space DA of the practitioner D, a three-dimensional movement space SA of the operator S, a three-dimensional movement space NA of the nurse N supporting the treatment. The C-arm 47 is rotated in consideration of preventing the X-ray irradiator 45 and the X-ray detector 46 from entering the three-dimensional movement spaces DA, SA and NA. Therefore, if a distance between the X-ray irradiator 45 or the X-ray detector 46 held by the C-arm 47 in an X-ray irradiating direction, and the three-dimensional movement space DA, SA or NA is long, a suitability level of the index "efficiency of treatment" in the X-ray irradiating direction is high.

According to at least one embodiment, it is possible to provide an X-ray irradiating direction suitable for a procedure.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical apparatus comprising control circuitry configured to:
   acquire a prior three-dimensional cumulative dose distribution of an object;
   set a treatment target site to be treated with X-ray irradiation to the object;
   calculate, based on the prior three-dimensional cumulative dose distribution, a first distribution in which suitability levels are distributed on a coordinate system defined by a combination of two-axis rotation angles of an arm supporting an X-ray irradiator and an X-ray detector;
   calculate, based on position data of the treatment target site, a second distribution in which suitability levels are distributed on the coordinate system defined by the combination of the two-axis rotation angles of the arm; and
   determine, based on the first and second distributions, an X-ray irradiating direction for performing the X-ray irradiation.

2. The medical apparatus according to claim 1, wherein:
   the first distribution corresponds to the combination in which cumulative doses are equal to or less than a predetermined threshold value at any position of the prior three-dimensional cumulative dose distribution; and
   the second distribution is based on a visibility of the treatment target site in an X-ray image when the X-ray image is generated based on at least a part of the X-ray irradiation.

3. The medical apparatus according to claim 2, wherein the control circuitry is configured to calculate the visibility of the treatment target site in the X-ray image, based on not only a structure of the treatment target site but also a content of a procedure for treating the treatment target site.

4. The medical apparatus according to claim 2, wherein the control circuitry is configured to:
   calculate the suitability levels of the visibility of the treatment target site, based on sizes of the treatment target site viewed from the respective combinations of the two-axis rotation angles of the aim.

5. The medical apparatus according to claim 1, wherein the control circuitry is configured to:
   transmit data to a display unit configured to display the first and second distributions.

6. The medical apparatus according to claim 1, wherein the control circuitry is configured to transmit data to a display unit configured to display a maximum of the suitability levels of the first distribution, a maximum of the suitability levels of the second distribution, and a combination of the two-axis rotation angles of the arm corresponding to the each maximum suitability level.

7. The medical apparatus according to claim 1, wherein the control circuitry is configured to:
   calculate, based on exposure dose of a surrounding person, a third distribution in which suitability levels are distributed on a coordinate system defined by the combination of the two-axis rotation angles of the arm; and
   determine, based on the first, second and third distributions, the X-ray irradiating direction.

8. An X-ray system comprising:
   the medical apparatus according to claim 1; and
   an X-ray apparatus configured to perform imaging with a specific combination of two-axis rotation angles of an arm determined by the medical apparatus, or a specific X-ray irradiating direction after being changed from the X-ray irradiating direction determined by the medical apparatus.

9. The X-ray system according to claim 8, wherein the control circuitry is configured to:
   transmit data to a display unit configured to display a suitability level corresponding to the specific X-ray irradiating direction.

10. The medical apparatus according to claim 1, wherein one of two-axis rotation angles is an angle of axial rotation along a longitudinal direction of a table, and the other is an angle of axial rotation along a lateral direction of the table, the table being for placing the object.

11. A medical apparatus comprising control circuitry configured to:
    acquire a prior three-dimensional cumulative dose distribution of an object;
    set a treatment target site to be treated with X-ray irradiation to the object;
    calculate, based on the prior three-dimensional cumulative dose distribution, a first suitability level corresponding to a combination of two-axis rotation angles of an arm, the arm supporting an X-ray irradiator and an X-ray detector;
    calculate, based on position data of the treatment target site, a second suitability level corresponding to the combination of the two-axis rotation angles of the arm;
    calculate, based on surrounding radiation dose of a surrounding person, a third suitability level; and
    determine, based on the first, second and third suitability levels, an X-ray irradiating direction for performing the X-ray irradiation,
    wherein the control circuitry is configured to transmit data to a display unit configured to display the first, second and third suitability levels, using a radar chart having the first suitability, the second suitability and the third suitability as axes.

12. A medical apparatus comprising control circuitry is configured to:
    acquire a prior three-dimensional cumulative dose distribution of an object;
    set a treatment target site to be treated with X-ray irradiation to the object;
    calculate, based on the prior three-dimensional cumulative dose distribution, a first suitability level as a first primary suitability level corresponding to a combination of two-axis rotation angles of an arm supporting an X-ray irradiator and an X-ray detector;
    calculate, based on position data of the treatment target site, a second suitability level as a second primary suitability level corresponding to the combination of the two-axis rotation angles of the arm;
    calculate a secondary suitability level, based on the first and second primary suitability levels; and
    transmit data to a display unit configured to display the secondary suitability level.

13. The medical apparatus according to claim 12, wherein the control circuitry is configured to calculate the secondary suitability level by adding or weighting the first and second primary suitability levels.

14. The medical apparatus according to claim 12, wherein the control circuitry is configured to:

calculate, based on surrounding radiation dose of a surrounding person, a third suitability level as a third primary suitability level; and calculate the secondary suitability level, based on the first, second and third primary suitability levels, corresponding to the combination of the two-axis rotation angles of the arm.

15. The medical apparatus according to claim 12, wherein the control circuitry is configured to display, on the display, the secondary suitability level in order.

* * * * *